United States Patent
Leng et al.

(10) Patent No.: US 11,631,171 B2
(45) Date of Patent: Apr. 18, 2023

(54) AUTOMATED DETECTION AND ANNOTATION OF PROSTATE CANCER ON HISTOPATHOLOGY SLIDES

(71) Applicant: Regents of the University of Minnesota, Minneapolis, MN (US)

(72) Inventors: Ethan Yize Leng, Minneapolis, MN (US); Gregory John Metzger, Lake Elmo, MN (US); Joseph S. Koopmeiners, Edina, MN (US); Jonathan Henriksen, Seattle, WA (US); Stephen C. Schmechel, Longboat Key, FL (US)

(73) Assignee: Regents of the University of Minnesota, Minneapolis, MN (US)

( * ) Notice: Subject to any disclaimer, the term of this patent is extended or adjusted under 35 U.S.C. 154(b) by 479 days.

(21) Appl. No.: 16/736,914

(22) Filed: Jan. 8, 2020

(65) Prior Publication Data
US 2020/0250817 A1    Aug. 6, 2020

Related U.S. Application Data

(60) Provisional application No. 62/790,523, filed on Jan. 10, 2019.

(51) Int. Cl.
*G06K 9/00*    (2022.01)
*G06T 7/00*    (2017.01)
(Continued)

(52) U.S. Cl.
CPC ..... *G06T 7/0012* (2013.01); *G01N 33/57434* (2013.01); *G16H 30/20* (2018.01);
(Continued)

(58) Field of Classification Search
CPC . G06T 2207/20081; G06T 2207/20084; G06T 2207/10056; G06T 2207/10061;
(Continued)

(56) References Cited

U.S. PATENT DOCUMENTS 5,800,353 A    9/1998    McLaurin, Jr.
6,004,267 A    12/1999    Tewari et al.
(Continued)

FOREIGN PATENT DOCUMENTS

CN    103699904 A    4/2014
CN    104794426 A    7/2015
(Continued)

OTHER PUBLICATIONS

Giannini et al., "A Novel and Fully Automated Registration Method for Prostate Cancer Detection Using Multiparametric Magnetic Resonance Imaging," Journal of Medical Imaging and Health Informatics, vol. 5, No. 6, Nov. 2015, 12 pp.
(Continued)

*Primary Examiner* — Atiba O Fitzpatrick
(74) *Attorney, Agent, or Firm* — Shumaker & Sieffert, P.A.

(57) ABSTRACT

Automated, machine learning-based systems are described for the analysis and annotation (i.e., detection or delineation) of prostate cancer (PCa) on histologically-stained pathology slides of prostatectomy specimens. A technical framework is described for automating the annotation of predicted PCa that is based on, for example, automated spatial alignment and colorimetric analysis of both H&E and IHC whole-slide images (WSIs). The WSIs may, as one example, be stained with a particular triple-antibody cocktail against high-molecular weight cytokeratin (HMWCK), p63, and α-methylacyl CoA racemase (AMACR).

21 Claims, 14 Drawing Sheets
(12 of 14 Drawing Sheet(s) Filed in Color)

(51) Int. Cl.
G16H 50/20 (2018.01)
G16H 30/20 (2018.01)
G01N 33/574 (2006.01)
(52) U.S. Cl.
CPC ... *G16H 50/20* (2018.01); *G06T 2207/10056* (2013.01); *G06T 2207/30024* (2013.01); *G06T 2207/30081* (2013.01)
(58) Field of Classification Search
CPC . G06T 2207/30024; G06T 2207/30096; G06T 2207/30081; G06T 7/10–194; G06T 2207/20112; G06T 2207/30242; G06T 2219/004; G06T 2207/10024; G06T 7/0012–0016; G06T 2207/30004–30104; G06T 2207/20021; G06T 7/30–38; G06T 2219/2004; G06T 2207/20212; G06T 2207/20221; G06K 9/6256; G06K 9/6257; G06K 9/6259; G06K 9/6224; G06V 10/70; G06V 10/82; G06V 10/774–7796; G06V 20/693; G06V 20/695; G06V 20/698; G06V 2201/04; G06V 20/69; G06V 2201/032; G06V 40/162; G06V 20/80; G06V 20/70; G06V 2201/03; G06V 10/759; G06V 30/19013; G06N 3/02–126; G01N 33/57434; G01N 1/30–2001/317; A61B 5/7485; A61B 2090/364; G16H 50/20

See application file for complete search history.

(56) References Cited

U.S. PATENT DOCUMENTS

| | | | |
|---|---|---|---|
| 7,245,748 B2 | 7/2007 | Degani et al. | |
| 7,831,293 B2 | 11/2010 | Ellis et al. | |
| 8,295,575 B2 | 10/2012 | Feldman et al. | |
| 8,386,012 B2 | 2/2013 | Fehre et al. | |
| 8,518,650 B2 | 8/2013 | Mitchell et al. | |
| 8,548,562 B2 | 10/2013 | Trachtenberg et al. | |
| 8,718,350 B2 | 5/2014 | Metzger et al. | |
| 9,858,665 B2 | 1/2018 | Metzger et al. | |
| 2005/0186642 A1* | 8/2005 | Tacha | G01N 33/57484 435/7.9 |
| 2007/0232882 A1 | 10/2007 | Glossop et al. | |
| 2008/0214950 A1 | 9/2008 | Fehre et al. | |
| 2010/0169024 A1 | 7/2010 | Madabhushi et al. | |
| 2010/0329529 A1 | 12/2010 | Feldman et al. | |
| 2012/0257811 A1* | 10/2012 | Metzger | G06V 20/69 382/133 |
| 2013/0064439 A1 | 3/2013 | Khurd et al. | |
| 2013/0196868 A1 | 8/2013 | Lebowitz et al. | |
| 2013/0287283 A1 | 10/2013 | Kamath et al. | |
| 2014/0073907 A1 | 3/2014 | Kumar et al. | |
| 2014/0185891 A1* | 7/2014 | Schoenmeyer | G06T 11/206 382/128 |
| 2014/0303041 A1 | 10/2014 | Hayes et al. | |
| 2015/0201910 A1 | 7/2015 | Zhao et al. | |
| 2015/0301054 A1* | 10/2015 | Liao | G01N 33/57434 435/325 |
| 2015/0317431 A1 | 11/2015 | Gronberg et al. | |
| 2016/0292855 A1 | 10/2016 | Metzger et al. | |
| 2017/0261584 A1 | 9/2017 | James et al. | |
| 2018/0156883 A1 | 6/2018 | Oz et al. | |
| 2018/0182099 A1* | 6/2018 | Lesniak | G06K 9/6256 |
| 2020/0126222 A1* | 4/2020 | Barnes | G06V 10/771 |
| 2020/0211189 A1* | 7/2020 | Yip | G06T 7/0012 |
| 2020/0214619 A1 | 7/2020 | Leng et al. | |
| 2020/0226462 A1* | 7/2020 | Maddison | G01N 33/53 |
| 2020/0372235 A1* | 11/2020 | Peng | G01N 1/30 |
| 2020/0388028 A1* | 12/2020 | Agus | G16H 30/40 |
| 2020/0394825 A1* | 12/2020 | Stumpe | G06V 10/82 |
| 2021/0150701 A1* | 5/2021 | Thagaard | G06V 20/698 |
| 2021/0201485 A1* | 7/2021 | Chukka | G06V 20/698 |
| 2022/0058839 A1* | 2/2022 | Chang | G06T 11/00 |

FOREIGN PATENT DOCUMENTS

| | | |
|---|---|---|
| CN | 105184798 A | 12/2015 |
| CN | 103593843 B | 4/2016 |
| CN | 106204561 A | 12/2016 |
| CN | 106778005 A | 5/2017 |
| CN | 107133638 B | 1/2020 |
| EP | 2545527 B1 | 7/2014 |

OTHER PUBLICATIONS

Allam et al., "Interobserver Variability in the Diagnosis of High-Grade Prostatic Intraepithelial Neoplasia and Adenocarcinoma,"Modern Pathology, vol. 9, No. 7, Jul. 1996, 10 pp.

Anderson et al., "Multiparametric MRI identifies and stratifies prostate cancer lesions: Implications for targeting intraprostatic targets," Brachytherapy, vol. 13, No. 3, Jan. 2014, 7 pp.

Araujo et al., "Classification of breast cancer histology images using Convolutional Neural Networks," PLoS One, vol. 12, No. 6, Jun. 2017, 14 pp.

Arevalo et al., "An unsupervised feature learning framework for basal cell carcinoma image analysis," Artificial Intelligence in Medicine, vol. 64, No. 2, Jun. 2015, 15 pp.

Barentsz et al., "ESUR prostate MR guidelines 2012," Eur Radiol, Feb. 10, 2012, 12 pp.

Brockman et al., "Nomogram Predicting Prostate Cancer-specific Mortality for Men with Biochemical Recurrence After Radical Prostatectomy," European Urology, vol. 67, No. 6, Jun. 2015, 17 pp.

Chan et al., "Detection of prostate cancer by integration of line-scan diffusion, T2-mapping and T2-weighted magnetic resonance imaging; a multichannel statistical classifier," Med. Phys., vol. 30, No. 9, Sep. 2003, 9 pp.

Chappelow et al., "Elastic registration of multimodal prostate MRI and histology via multiattribute combined mutual information," Medical Physics—The International Journal of Medical Physics Research and Practice, vol. 38, No. 4, Apr. 2011, 14 pp.

Chappelow et al., "Improving supervised classification accuracy using non-rigid multimodal image registration: detecting prostate cancer," Proceedings of SPIE, vol. 6915, Mar. 2018, 12 pp.

Cheung et al., "Using manual prostate contours to enhance deformable registration of endorectal MRI," Computer Methods and Programs in Biomedicine, vol. 108, No. 1, Oct. 2012, 8 pp.

Cruz-Roa et al., "Accurate and Reproducible Invasive Breast Cancer Detection in Whole-Slide Images: A Deep Learning Approach for Quantifying Tumor Extent," Scientific Reports, vol. 7, Article No. 46450, Apr. 2017, 14 pp.

Dabir et al., "Comparative Analysis of three- and two-antibody Cocktails to AMACR and Basal Cell Markers for the Immunohistochemical Diagnosis of Prostate Carcinoma," Diagnostic Pathology, vol. 7, Article No. 81, Jul. 2012, 6 pp.

Delongchamps et al., "Multiparametric magnetic resonance imaging for the detection and localization of prostate cancer: combination of T2-weighted, dynamic contrast-enhanced and diffusion-weighted imaging," BJU International, vol. 107, No. 9, May 2011, 8 pp.

DeLuca et al., "A Fully Automatic Method to Register the Prostate Gland on T2-weighted and EPI-DWI Images," 2011 Annual International Conference of the IEEE Engineering in Medicine and Biology Society, Aug. 2011, 4 pp.

Dickinson et al., "Magnetic Resonance Imaging for the Detection, Localisation, and Characterisation of Prostate Cancer: Recommendations from a European Consensus Meeting," European Urology, vol. 59, Dec. 21, 2010, 18 pp.

Divrik et al., "Increasing the number of biopsies increases the concordance of Gleason scores of needle biopsies and prostatectomy specimens," Urologic Oncology: Seminars and Original Investigations, vol. 25, No. 5, Sep.-Oct. 2007, 7 pp.

Efron et al., "An Introduction to the Bootstrap," CRC Press, 1998, 11 pp. (Applicant points out, in accordance with MPEP 609.04(a),

(56) References Cited

OTHER PUBLICATIONS that the year of publication, 1998, is sufficiently earlier than the effective U.S. filing date, so that the particular month of publication is not in issue.).
Eichelberger et al., "Predicting Tumor Volume in radical Prostatectomy Specimens From Patients With Prostate Cancer," Am J Clin Pathol, vol. 120, No. 3, Sep. 2003, 6 pp.
Epstein et al., "A Contemporary Prostate Cancer Grading System: A Validated Alternative to the Gleason Score," European Urology, vol. 69, No. 3, Mar. 2016, 19 pp.
Friedman et al., "Regularization Paths for Generalized Linear Models via Coordinate Descent," Journal of Statistical Software, vol. 33, No. 1, Jan. 2010, 22 pp.
Garcia-Reyes et al., "Detection of prostate cancer with multiparametric MRI (mpMRI): effect of dedicated reader education on accuracy and confidence of index and anterior cancer diagnosis," Abdom Imagine, vol. 41, No. 1, Jan. 2015, 20 pp.
Ghosh et al., "A Genetic Algorithm-Based Level Set Curve Evolution for Prostate Segmentation on Pelvic CT and MRI Images," Chapter 6 in Biomedical Image Analysis and Machine Learning, Technologies: Applications and Techniques, 2010, 25 pp. (Applicant points out, in accordance with MPEP 609.04(a), that the year of publication, 2010, is sufficiently earlier than the effective U.S. filing date, so that the particular month of publication is not in issue.).
Giannini et al., "A fully automatic computer aided diagnosis system for peripheral zone prostate cancer detection using multi-parametric magnetic resonance imaging," Computerized Medical Imaging and Graphics, vol. 46, Dec. 2015, 8 pp.
Giannini et al., "A prostate CAD system based on multiparametric analysis of DCE T1-w, and DW automatically registered images," Proceedings of SPIE—The International Society for Optical Engineering, vol. 8670, Feb. 2013, 7 pp.
Gibbs et al., "Comparison of Quantitative T2 Mapping and Diffusion-Weighted Imagine in the Normal and Pathologic Prostate," vol. 46, No. 6, Dec. 2001, 5 pp.
Glass et al., "SIMPLE: A Sequential Immunoperoxidase Labeling and Erasing Method," Journal of Histochemistry and Cytochemistry, vol. 57, No. 10, Oct. 2009, 7 pp.
Guo et al., "Intraductal Carcinoma of the Prostate on Needle Biopsy: Histologic Features and Clinical Significance," Modern Pathology: An Official Journal of the United States and Canadian Academy of Pathology, Inc., vol. 19, No. 12, Dec. 2006, 8 pp.
Gurcan et al.. "Histopathological Image Analysis: A Review," IEEE Reviews in Biomedical Engineering, vol. 2, Oct. 2009, 25 pp.
Hao et al., "Nonrigid Registration of Prostate Diffusion-Weighted MRI," Journal of Healthcare Engineering, vol. 2017, Article ID 92963 54, Jun. 2017, 12 pp.
Hedgire et al., "Multiparametric magnetic resonance imaging of prostate cancer," Indian J Radiol Imaging, vol. 22, No. 3, Jul.-Sep. 2012, 24 pp.
Heidenreich et al., "EAU Guidelines on Prostate Cancer. Part 1: Screening, Diagnosis, and Local Treatment With Curative Intent— Update 2013," European Urology, vol. 65, No. 1, Jan. 2014, 14 pp.
Herawi et al., "Immunohistochemical Antibody Cocktail Staining (p63/HMWCK/AMACR) of Ductal Adenocarcinoma and Gleason Pattern 4 Cribriform and Noncribriform Acinar Adenocarcinomas of the Prostate," The American Journal of Surgical Pathology, vol. 31, No. 6, Jun. 2007, 6 pp.
Homer et al., "Driven-Equilibrium Single-Pulse Observation of T1 Relaxation/ A Reevaluation of a Rapid "New," Method for Determining NMR Spin-Lattice Relaxation Times," Journal of Magnetic Resonance, vol. 63, No. 2, Jun. 15, 1985, 11 pp.
Humphrey, P.A., "Diagnosis of adenocarcinoma in prostate needle biopsy tissue," Journal of Clinical Pathology, vol. 60, No. 1, Jan. 2007, 8 pp.
Jin et al., "Detection of Prostate Cancer with Multiparametric MRI Utilizing the Anatomic Structure of the Prostate," Statistics in Medicine, vol. 37, No. 22, Sep. 2018, 28 pp.

Kalavagunta et al., "Analysis of Quantitative MRI and Pathology based on Co-registered Regions of Prostate Cancer," Proc. Intl. Soc. Mag. Reson. Med., vol. 20, 2012, 1 pp. (Applicant points out, in accordance with MPEP 609.04(a), that the year of publication, 2012, is sufficiently earlier than the effective U.S. filing date, so that the particular month of publication is not in issue.).
Kalavagunta et al., "Registration of In Vivo Prostate MRI and Pseudo-Whole Mount Histology Using Local Affine Transformations Guided by Internal Structures (LATIS)," Journal of Magnetic Resonance Imaging: JMRI, vol. 41, No. 4, Apr. 2015, 11 pp.
Kalavagunta, "Multiparametric MRI and Digital Pathology of Prostate Cancer, An Image Registration based Correlation Study," Nov. 2013; Donald Gleason Conference on Prostate and Urologic Cancers University of Minnesota, Department of Radiology, 1 pp.
Kalvagunta et al., "Pixel-Wise Multi-parametric Assessment of Prostate Cancer from Co-registered regions of Pathologically defined Disease," Proc. Intl. Soc. Mag. Reson. Med., vol. 22, 2014, 1 pp. (Applicant points out, in accordance with MPEP 609.04(a), that the year of publication, 2014, is sufficiently earlier than the effective U.S. filing date,so that the particular month of publication is not in issue.).
Kather et al.. "Multi-class texture analysis in colorectal cancer histology," Scientific Reports, vol. 6, Article 27988, Jun. 2016, 11 pp.
Khosravi et al., "Deep Convolutional Neural Networks Enable Discrimination of Heterogeneous Digital Pathology Images," E. Bio Medicine, vol. 27, Jan. 2018, 12 pp.
Kim et al., "Localization of Prostate Cancer Using 3T Mri, Comparison of T2-Weighted and Dynamic Contrast-Enhanced Imaging," J Comput Assist Tomogr, vol. 30, No. 1, Jan.-Feb. 2006, 5 pp.
Kothari et al., "Removing Batch Effects From Histopathological Images for Enhanced Cancer Diagnosis," IEEE Journal of Biomedical and Health Informatics, vol. 18, No. 3, May 2014, 23 pp.
Krajewska et al., "Image Analysis Algorithms for Immunohistochemical Assessment of Cell Death Events and Fibrosis in Tissue Sections," Journal of Histochemistry and Cytochemistry, vol. 57, No. 7, Jul. 2009, 15 pp.
Kuefer et al., "Methylacyl-CoA Racemase: Expression Levels of this Novel Cancer Biomarker Depend on Tumor Differentiation," The American Journal of Pathology, vol. 161, No. 3, Sep. 2002, 8 pp.
Kurhanewicz et al., "Multiparametric magnetic resonance imaging in prostate cancer: present and future," Curr Opin Urol, vol. 18, No. 1, Jan. 2008, 7 pp.
Kwak et al., "Automated prostate cancer detection using T2-weighted and high-b-value diffusion-weighted magnetic resonance imaging," Medical Physics—The International Journal of Medical Physics Research and Practice, vol. 42, No. 5, May 2015, 11 pp.
Langer et al., "Prostate Cancer Detection With Multi-parametric MRI: Logistic Regression Analysis of Quantitative T2, Diffusion-Weighted Imaging, and Dynamic Contrast-Enhanced MRI," Journal of Magnetic Resonance Imaging, vol. 30, No. 2, Aug. 2009, 8 pp.
Lavasani et al., "Automatic Prostate Cancer Segmentation Using Kinetic Analysis in Dynamic Contrast-Enhanced MRI," Journal of Biomedical & Physics Engineering, vol. 8, No. 1, Mar. 2018, 10 pp.
Le Bihan et al., "Separation of Diffusion and Perfusion in Intravoxel Incoherent Motion MR Imaging," Radiology, vol. 168, No. 2, Aug. 1988, 9 pp.
Lemaitre et al., "Computer-Aided Detection and diagnosis for prostate cancer based on mono and multiparametric MRI: a Review," Computers in Biology and Medicine, vol. 60, May 2015, 24 pp.
Leng et al., "Estimation of prostate cancer distribution on pathology slides via image analysis of IHC-stained slides," Abstract presented at the International Society for Magnetic Resonance in Medicine (ISMRM) 2018 conference, accepted Feb. 2, 2018 and presented Jun. 9, 2018, 3 pp.
Leng et al., "Colorimetric Image Analysis of H&E and IHC Slides for Automated Pathologic Annotation of Prostate Cancer," ISMRM Workshop on Advanced in Multiscale Cancer Detection: From Micro to Macro, Dublin, Ireland, 2018, 1 pp. (Applicant points out, in accordance with MPEG 609.04(a), that the year of publication, 2018, is sufficiently earlier than the effective U.S. filing date, so that the particular month of publication is not in issue.).

(56) References Cited

OTHER PUBLICATIONS

Li et al., "Improved noninvasive prostate cancer assessment using multiparametric magnetic resonance imaging," 2016 IEEE 13th International Symposium on Biomedical Imaging (ISBI), Apr. 2016, 5 pp.
Liney et al., "Comparison of Conventional Single Echo and Multi-Echo Sequences with a Fast Spin-Echo Sequence for Quantitative T2 Mapping: Application to the Prostate," JMRI, Jul. 1996, 5 pp.
Liney et al., "In Vivo Quantification of Citrate Concentration and Water T2 Relaxation Time of the Pathologic Prostate Gland using 1H MRS and MRI," Magnetic Resonance Imaging, vol. 15, No. 10, Jul. 20, 1997, 10 pp.
Litjens et al., "Computer-Aided Detection of Prostate Cancer in MRI," IEEE Transactions on Medical Imaging, vol. 33, No. 5, May 2014, 10 pp.
Litjens et al., "Deep Learning as a Tool for Increased Accuracy and Efficiency of Histopathological Diagnosis," Scientific Reports, vol. 6, Article No. 26286, May 2016, 11 pp.
Lotan et al., "Cytoplasmic PTEN Protein Loss Distinguishes Intraductal Carcinoma of the Prostate from High-Grade Prostatic Intraepithelial Neoplasia," Modern Pathology, vol. 26, No. 4, Apr. 2013, 17 pp.
Lughezzani et al., "Multicenter European External Validation of a Prostate Health Index-based Nomogram for Predicting Prostate Cancer at Extended Biopsy," European Urology, vol. 66, No. 5, Nov. 2014, 7 pp.
Luo et al., "alpha-Methylacyl-CoA Racemase: A New Molecular Marker for Prostate Cancer," Cancer Research, vol. 62, No. 8, Apr. 2002, 7 pp.
MacEnko et al., "A method for normalizing histology slides for quantitative analysis," In IEEE International Symposium on Biomedical Imaging: From Nano to Macro, Jun. 2009, 4 pp.
Makni et al., "Combining a deformable model and a probabilistic framework for an automatic 3D segmentation of prostate on MRI," International Journal of Computer Assisted Radiology and Surgery, vol. 4, No. 181, Dec. 2008, 8 pp.
Marin et al., "Prostate cancer: Computer-Aided Diagnosis on Multiparametric MRI," Proceedings in SPIE, vol. 10572, Nov. 2017, 7 pp.
Martin et al., "Automated Segmentation of the Prostate in 3D MR images Using a Probabilistic Atlas and a Spatially Constrained Deformable Model," Medical Physics—The International Journal of Medical Physics Research and Practice, vol. 37, No. 4, Mar. 2010, 21 pp.
Matulewicz et al., "Anatomic segmentation improves prostate cancer detection with artificial neural networks analysis of 1H MRSI," J Magn Reson Imaging, vol. 40, No. 6, Dec. 2014, 18 pp.
McNeal et al., "Capsular Penetration in Prostate Cancer. Significance for Natural History and Treatment," The American Journal of Surgical Pathology, vol. 14, No. 3, Mar. 1990, 8 pp.
Metzger et al., "Detection and grading of prostate cancer using model-based spectral fitting," Proc. Intl. Soc. Mag. Reson. Med., vol. 22, 2014, 1 pp. (Applicant points out, in accordance with MPEP 609.04(a), that the year of publication, 2014, is sufficiently earlier than the effective U.S. filing date, so that the particular month of publication is not in issue.).
Metzger et al., "Detection of Prostate Cancer: Quantitative Multiparametric MR Imaging Models Developed Using Registered Correlative Histopathology," Radiology, vol. 279, No. 3, Jun. 2016, 12 pp.
Metzger et al., "Development of Multigene Expression Signature Maps at the Protein level from Digitized Immunohistochemistry Slides," PLos ONE, vol. 7, No. 3, Mar. 2012, 12 pp.
Montironi et al., "Gleason grading of prostate cancer in needle biopsies or radical prostatectomy specimens: contemporary approach, current clinical significance and sources of pathology discrepancies," BJU International, vol. 95, No. 8, Jun. 2005, 7 pp.
Montironi et al., "Prostatic Intraepithelial Neoplasia: Its Morphological and Molecular Diagnosis and Clinical Significance," BJU International, vol. 108, Nov. 2011, 6 pp.
Morton et al., "Screening Mammograms: Interpretation with Computer-aided Detection—Prospective Evaluation," Radiology, vol. 23 9, No. 2, May 2006, 9 pp.
Mullerad et al., "Prostate Cancer: Detection of Extracapsular Extension by Genitourinary/ and General Body Radiologists at MR Imaging," vol. 232, No. 1, Jul. 2004, 7 pp.
Nam et al., "JPStitch 2.0: a Software for Volumetric Reconstruction and Analysis of Digitized Pathology," University of Minnesota, Nov. 2013; Donald Gleason Conference on Prostate and Urologic Cancers, Minneapolis, MN, 1 pp.
Ng et al., "Is Triple Immunostaining with 34betaE12, p63, and Racemase in Prostate Cancer Advantageous? A Tissue Microarray Study," American Journal of Clinical Pathology, vol. 127, No. 2, Feb. 2007, 6 pp.
Niaf et al., "Computer-aided diagnosis of prostate cancer in the peripheral zone using multiparametric MRI," Physics in Medicine and Biology, vol. 57, No. 23, Jun. 21, 2012, 19 pp.
Orczyk et al., "Imaging of prostate cancer: a platform for 3D co-registration of in-vivo MRI ex-vivo MRI and pathology," Proc SPIE, Feb. 23, 2012, 18 pp.
Orczyk et al., "Preliminary/ Experience With a Novel Method of Three-Dimensional Co-Registration of Prostate Cancer Digital Histology and in Vivo Multiparametric MRI," Clinical Radiology, vol. 68, No. 12, Aug. 2013, 12 pp.
Parker et al., "Experimentally-Derived Functional Form for a Population-Averaged High-Temporal-Resolution Arterial Input Function for Dynamic Contrast-Enhanced MRI," Magnetic Resonance in Medicine, vol. 56, No. 5, Nov. 2006, 8 pp.
Pedregosa et al., "Scikit-learn: Machine Learning in Python," Journal of Machine Learning Research, vol. 12, No. 85, Oct. 2011, 6 pp.
Puech et al., "Computer-assisted diagnosis of prostate cancer using DCE-MRI data: design, implementation and preliminary results," Int J CARS, vol. 4, Oct. 21, 2008, 10 pp.
Rizzardi et al., "Elevated HA and HMMR are Associated with Biochemical Failure in Patients with Intermediate Grade Prostate Tumors," Cancer, vol. 120, No. 12, Jun. 2014, 10 pp.
Rizzardi et al., "Evaluation of Protein Biomarkers of Prostate Cancer Aggressiveness," BMC Cancer, vol. 14, Article No. 244, Apr. 2014, 14 pp.
Rizzardi et al., "Quantitative Comparison of Immunohistochemical Staining Measured by Digital Image Analysis Versus Pathologist Visual Scoring," Diagnostic Pathology, vol. 7, Article No. 42, Jun. 2012, 10 pp.
Rosenkrantz et al., "Prostate Cancer Localization Using Multiparametric MR Imagine: Comparison of Prostate Imaging Reporting and Data System (PI-RADS) and Likert Scales," Radiology, vol. 269, No. 2, Nov. 2013, 11 pp.
Rubin et al., "alpha-Methylacyl Coenzyme A Racemase as a Tissue Biomarker for Prostate Cancer," Jama, vol. 287, No. 13, Apr. 2002, 9 pp.
Ruprecht et al., "MRI of the prostate: Interobserver agreement compared with histopathologic outcome after radical prostatectomy," European Journal of Radiology, vol. 81, Dec. 28, 2010, 5 pp.
Sanda et al., "Quality of Life and Satisfaction with Outcome among Prostate-Cancer Survivors," The New England Journal of Medicine, vol. 358, No. 12, Mar. 20, 2008, 12 pp.
Shah et al., "Atypical Cribriform Lesions of the Prostate: Clinical Significance, Differential Diagnosis and Current Concept of Intraductal Carcinoma of the Prostate," Advances in Anatomic Pathology, vol. 19, No. 4, Jul. 2012, 9 pp.
Shah et al., "Decision Support System for Localizing Prostate Cancer Based on Multiparametric Magnetic Resonance Imaging," Medical Physics, The International Journal of Medical Physics Research and Practice, vol. 39, No. 7, Jun. 2002, 11 pp.
Sharma et al., "Deep convolutional neural networks for automatic classification of gastric carcinoma using whole slide images in digital histopathology," Computerized Medical Imaging and Graphics: The Official journal of the Computerized Medical Imaging Society, vol. 61, Nov. 2017, 12 pp.
Siegel et al., "Cancer Statistics, 2017," CA Cancer Journal for Clinicians, vol. 67, No. 1, Jan./Feb. 2017, 24 pp.

(56) References Cited

OTHER PUBLICATIONS

Signoretti et al., "p63 is a prostate basal cell marker and is required for prostate development," The American Journal of Pathology, vol. 157, vol. 6, Dec. 2000, 7 pp.

Sobecki et al., "Feature Extraction Optimized for Prostate Lesion Classification," ICBBT '17: Proceedings of the 9th International Conference on Bioinformatics and Biomedical Technology, May 2017, 6 pp.

Stember et al., "Pilot Study of a Novel Tool for Input-Free Automated Identification of Transition Zone Prostate Tumors using T2- and Diffusion-Weighted Signal and Textural Features," Journal of Magnetic Resonance Imaging, vol. 40, No. 2, Aug. 2014, 5 pp.

Stephenson et al., "Postoperative Nomogram Predicting the 10-Year Probability of Prostate Cancer Recurrence After Radical Prostatectomy," Journal of Clinical Oncology: Official Journal of the American Society of Clinical Oncology, vol. 23, vol. 28, Oct. 2005, 8 pp.

Swindle et al., "Do margins matter? The prognostic significance of positive surgical margins in radical prostatectomy specimens," The Journal of Urology, vol. 179, May 2008, 5 pp.

Thoeny et al., "Diffusion-Weighted Imaging of the Parotid Gland: Influence of the Choice of b-Values on the Apparent Diffusion Coefficient Value," Journal of Magnetic Resonance Imaging, vol. 20, No. 5, Nov. 2004, 5 pp.

Tiwari et al., "Multimodal Wavelet Embedding Representation for data Combination (MaWERiC): Integrating Magnetic Resonance Imaging and Spectroscopy for Prostate Cancer Detection," NMR Biomed, vol. 25, No. 4, Apr. 2012, 30 pp.

Tofts et al., "Modeling Tracer Kinetics in Dynamic Gd-DTPA MR Imaging," JMRI, vol. 7, No. 1, Jan.-Feb. 1997, 11 pp.

Van der Loos et al., "Multiple Immunoenzyme Staining: Methods and Visualizations for the Observation with Spectral Imaging," Journal of Histochemistry and Cytochemistry', vol. 56, No. 4, Apr. 2008, 16 pp.

Viswanath et al., "Central Gland and Peripheral Zone Prostate Tumors Have Significantly Different Quantitative Imaging Signatures on 3 Tesla Endorectal, In Vivo T2-Weighted MR Imagery," Journal of Magnetic Resonance Imaging, vol. 36, No. 1, Jul. 2012, 12 pp.

Viswanath et al., "Integrating structural and functional imaging for computer assisted detection of prostate cancer on multi-protocol in vivo 3 Tesla MRI," Proceedings of SPIE—The International Society for Optical Engineering, vol. 7260, Feb. 2009, 21 pp.

Vos et al., "Automatic computer-aided detection of prostate cancer based on multiparametric magnetic resonance image analysis," Physics in Medicine and Biology, vol. 57, Mar. 6, 2012, 16 pp.

Vos et al., "Computer-assisted Analysis of Peripheral Zone Prostate Lesions Using T2-weighted and Dynamic Contrast Enhanced T1-weighted MRI," Physics in Medicine and Biology, vol. 55, No. 6, Mar. 2010, 16 pp.

Vos et al., Combining T2-weighted with dynamic MR images for computerized classification of prostate lesions, Proceedings of SPIE—The International Society for Optical Engineering, vol. 6915, Article No. 69150W, Mar. 2008, 8 pp.

Wang et al., "Searching for prostate cancer by fully automated magnetic resonance imaging classification: deep learning versus non-deep learning," Scientific Reports, vol. 7, Article # 15415, Nov. 2017, 8 pp.

Wei et al., "Comprehensive Comparison of Health-Related Quality of Life After Contemporary Therapies for Localized Prostate Cancer," Journal of Clinical Oncology, vol. 20, No. 2, Jan. 15, 2002, 10 pp.

Wibmer et al., "Haralick Texture Analysis of Prostate MRI: Utility for Differentiating Non-cancerous Prostate from Prostate Cancer and Differentiating Prostate Cancers with Different Gleason Scores," European Radiology, vol. 25, No. 10, Oct. 2015, 21 pp.

Wilt, "The Prostate Cancer Intervention Versus Observation Trial: VA/NCI/AHRQ Cooperative Studies Program #407 (PIVOT): Design and Baseline Results of a Randomized Controlled Trial Comparing Radical Prostatectomy With Watchful Waiting for Men With Clinically Localized Prostate Cancer," Journal of the National Cancer Institute Monographs, vol. 45, Dec. 2012, 7 pp.

Wojno et al., "The Utility of Basal Cell-Specific Anti-Cytokeratin Antibody (34βE12) in the Diagnosis of Prostate Cancer. A Review of 228 Cases," The American Journal of Surgical Pathology, vol. 19, No. 3, Mar. 1995, 10 pp.

Xiao et al., "Determining histology—MRI slice correspondences for defining MRI-based disease signatures of prostate cancer," Computerized Medical Imaging and Graphics, vol. 35, No. 7-8, Oct.-Dec. 2011, 11 pp.

Yamada et al., "Efficacy of Distortion Correction on Diffusion Imaging: Comparison of FSL Eddy and Eddy Correct Using 30 and 60 Directions Diffusion Encoding," PLoS One, vol. 9, No. 11, Nov. 2014, 9 pp.

Zhao et al., Anatomical Feature-Guided Mutual Information Registration of Multimodal Prostate MRI. In Yoshida H., Sakas G., Linguraru M.G. (eds) Abdominal Imaging. Computational and Clinical Applications. ABD-MICCAI 2011, Lecture Notes in Computer Science, vol. 7029. Springer, Berlin, Heidelberg Sep. 2012, 8 pp.

"Computer-aided diagnosis," WikipediA, accessed from https://en.wikipedia.org/wiki/Computer-aided_diagnosis, on May 27, 2020, 17 pp.

"Immunohistochemistry," WikipediA, accessed from indirect method of IHC staining on May 28, 2020, 9 pp.

"Pattern recognition," WikipediA, accessed from https://en.wikipedia.org/wiki/Pattern_recognition on May 27, 2020, 11 pp.

* cited by examiner

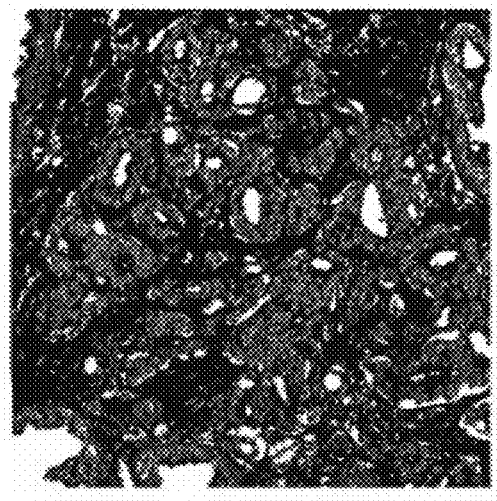
FIG. 4C Positive Pixel Count (nuclear)
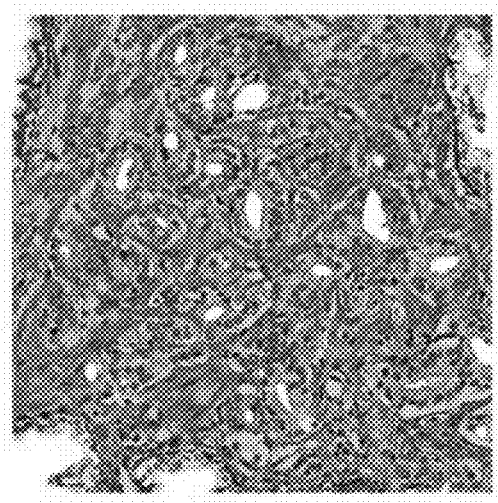
FIG. 4B Analysis square-level annotation
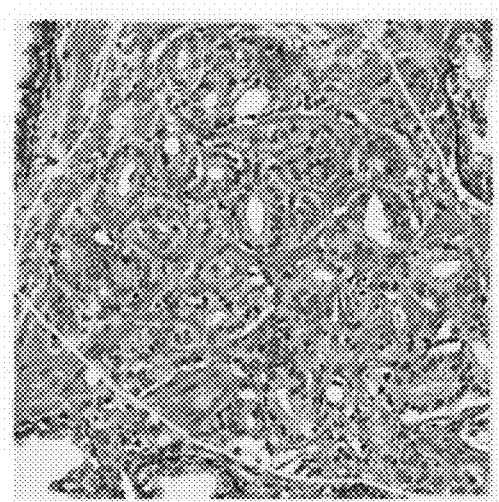
FIG. 4A Analysis square (H&E)
FIG. 4H Color Deconvolution (red)
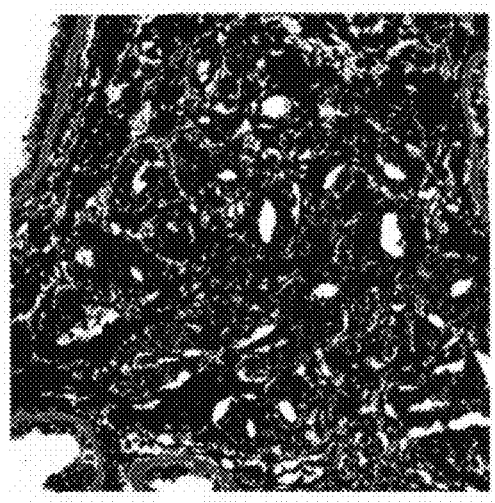
FIG. 4G Color Deconvolution (brown)
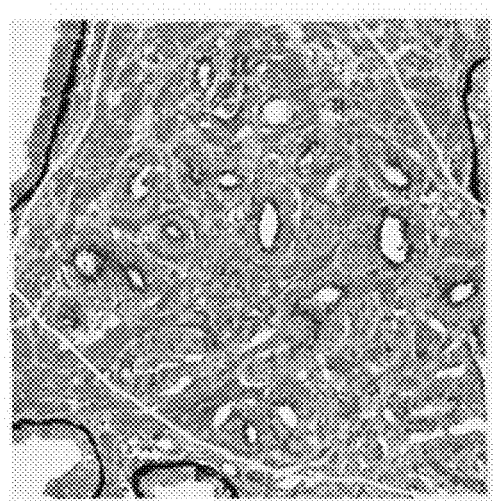
FIG. 4F Analysis square (IHC)

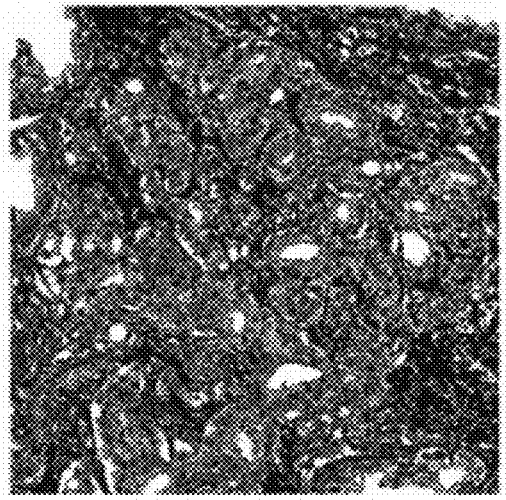
FIG. 4D Positive Pixel Count (cytoplasmic)
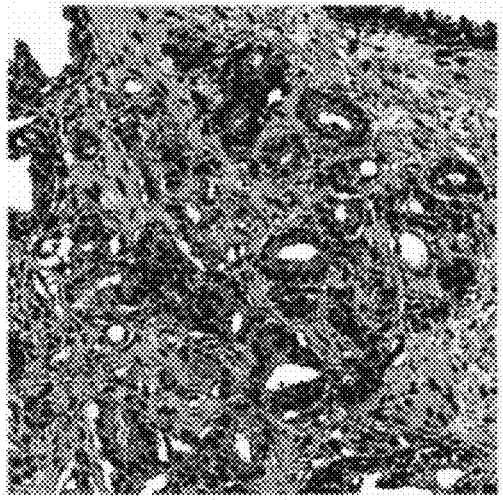
FIG. 4E Positive Pixel Count (stromal)
FIG. 4I Co-expression
| Feature | Value |
|---|---|
| (c) % Nuclei | 18.7% |
| (d) % Cytoplasm | 27.0% |
| (e) % Stroma | 40.6% |
| (f) OD × %Pos (brown) | 1.47 |
| (g) OD × %Pos (red) | 3.40 |
| (h) %Pos$_{CE}$ (brown) | 4.47% |
| (i) %Pos$_{CE}$ (red) | 17.7% |
FIG. 4J Table of derived features.

AUTOMATED DETECTION AND ANNOTATION OF PROSTATE CANCER ON HISTOPATHOLOGY SLIDES

This application claims the benefit of U.S. Provisional Patent Application No. 62/790,523 filed Jan. 10, 2019, the entire content being incorporated herein by reference.

STATEMENT REGARDING FEDERALLY SPONSORED RESEARCH OR DEVELOPMENT

This invention was made with government support under TL1-TR002493, UL1-TR002494, T32-GM008244, R01-CA155268, and P41-EB015894 awarded by the National Institutes of Health and W81XWH-15-1-0477 awarded by the Department of Defense. The government has certain rights in the invention.

BACKGROUND

Current diagnostic tests, including digital rectal exams (DRE), serum prostate specific antigen (PSA) and transrectal ultrasound (TRUS) guided biopsy, do not provide the information needed to confidently diagnose and manage prostate cancer (PCa) in an optimized, cost effective way. Serum PSA has low specificity, and random TRUS guided biopsy can result in underestimation of the presence, extent and grade of PCa. Uncertainty regarding the accurate assessment of grade and disease extent, particularly for men with apparent low-risk disease has limited the adoption of active surveillance despite the fact that it is considered by many to be the preferred initial management strategy for these men. This limitation has contributed to the significant overtreatment of prostate cancer with high costs to the healthcare system, and increased morbidity resulting in lower quality of life for many men.

SUMMARY

In general, the present disclosure describes systems and methods configured to apply predictive models trained to analyze whole slide images to identify prostate cancer from the colorimetric analysis of hematoxylin and eosin (H&E) and immunohistochemical (IHC) stained histopathological specimens, which may be specimens obtained from radical prostatectomy (RP). In some of the examples described below, this disclosure describes an automated, machine learning-based systems for the analysis and annotation (i.e., detection or delineation) of prostate cancer (PCa) on histologically-stained pathology slides of prostatectomy specimens. A technical architecture is described for automating the annotation of PCa that is based on, for example, automated colorimetric analysis of both H&E and IHC whole-slide images (WSIs). The WSIs may, as one example, be stained with a particular triple-antibody cocktail (combination) of primary antibodies against high-molecular weight cytokeratin (HMWCK), p63, and α-methylacyl CoA racemase (AMACR).

As described herein, predictive models, such as models applied by machine learning systems as one example, are trained to estimate the distribution of cancerous epithelium within slides. Experimental results indicated that the systems and techniques of the present disclosure achieved high levels of accuracy and generalized well to cancers of all grades. The systems and techniques described in this disclosure provide technical solutions for automation of the laborious process of cancer annotation, saving significant time while achieving cancer detection accuracy comparable to that of a trained pathologist.

Further, the systems and techniques described in this disclosure provide technical solutions that enable the expansion of ground truth data, which in turn increases the amount of modeling data available for training computer-aided diagnosis (CAD) systems models. For example, training predictive models employed for CAD systems can require a large amount of modeling data with correlated ground truth (i.e., the true pathologic state of the prostate). One technique for obtaining the ground truth utilizes the manual annotation of ex vivo prostatectomy specimens by trained pathologists, which is very time-consuming and may be prone to error. The systems and techniques described in this disclosure provide technical solutions for automation of the laborious process of cancer annotation, saving significant time while achieving cancer detection accuracy comparable to that of a trained pathologist. Further, the systems and techniques described in this disclosure provide technical solutions that enable the expansion of ground truth data, which in turn increases the amount of modeling data available for training CAD models.

In one example of the disclosure, automated cancer annotation is performed on information derived from both H&E and IHC WSIs, as opposed to from H&E WSIs alone. IHC staining with the aforementioned triple antibody cocktail provides additional information about the pathologic state of the tissue. Specifically, absence of staining for HMWCK and p63 as well as increased staining for AMACR are characteristic of PCa. Therefore, a model that uses information derived from analysis of IHC WSIs to annotate cancer may have improved accuracy.

In another example, this disclosure described the use of a unique set of predictors used for the regression model that is used to carry out automated cancer annotation. The techniques of this disclosure obtain the predictors for the regression model from the application of colorimetric algorithms to the H&E and IHC WSIs. These predictors help quantify the relative amounts of various cellular components within each analysis region, and therefore may be more readily interpretable (e.g., by pathologists or by end users). This is in contrast, for example, to a convolutional neural network (CNN), which would not explicitly calculate features from its analysis of H&E and IHC WSIs.

In another example of the disclosure, the ground truth used to train the regression model presented is more accurate than some other example techniques involving manual annotation. In examples of this disclosure, the ground truth used to train the regression model is derived from manual annotation of single analysis squares (taken from a number of WSIs) where individual components (e.g., cancer epithelium, stroma, glass) are delineated in much finer detail to arrive at the percentage of each component. Therefore, there is much higher confidence in the veracity of the ground truth.

In another example of the disclosure, the regression model returns as output the estimated percentage of cancer epithelium within each analysis region. This is in contrast to example techniques, where the output may be a binary label (cancer or non-cancer) for each analysis region. The estimated percentage of cancer epithelium is a more informative and flexible output, and by thresholding the percentage, the same binary label can be obtained for each analysis region.

In one example, this disclosure describes a method comprising receiving, by a computing device, a digitized scan comprising whole-slide images of two stained slides of a block of tissue, wherein the two stained slide comprise a first slide stained with hematoxylin & eosin (H&E) and a second slide stained with an immunohistochemical (IHC) antibody cocktail, spatially aligning, by the computing device, a first whole slide image of the first stained slide and a second whole slide image of the second stained slide, overlaying, by the computing device, analysis regions on the spatially aligned digitized scan, analyzing, by the computing device, one or more of the analysis regions of the spatially aligned digitized scan to quantify the staining, processing, by the computing device, the quantified staining of the digitized scan using a predictive model, wherein the output of the predictive model indicates areas of cancer within the digitized scan, and outputting, by the computing device, one or more indications of areas of cancer in the digitized scan.

In another example, this disclosure describes an apparatus comprising a computer-readable storage medium storing a digitized scan comprising whole-slide images of two stained slides of a block of tissue, wherein the two stained slide comprise a first slide stained with hematoxylin & eosin (H&E) and a second slide stained with an immunohistochemical (IHC) antibody cocktail, and a processor coupled to the computer-readable storage medium, wherein the processor is configured to receive the digitized scans of the slides, spatially align a first whole slide image of the first stained slide and a second whole slide image of the second stained slide, overlay analysis regions on the spatially aligned digitized scan, analyze one or more of the analysis regions of the spatially aligned digitized scan to quantify the staining, process the quantified staining of the digitized scan using a predictive model, wherein the output of the predictive model indicates areas of cancer within the digitized scan, and output one or more indications of areas of cancer in the digitized scan.

Example techniques of this disclosure may include one or more of the following processes:

1. Histological processing: Blocks of tissue are first obtained from prostatectomy specimens. Two adjacent sections of tissue blocks are then cut into slides and stained. One slide is stained with hematoxylin & eosin (H&E), and the other with an immunohistochemical (IHC) antibody cocktail containing antibodies against alpha-methylacyl CoA racemase (AMACR), high-molecular weight cytokeratin (HMWCK), and p63.

2. Digital processing and analysis: The stained slides are digitized to produce digital whole-slide images (WSIs). Corresponding adjacent H&E and IHC WSIs are registered (spatially aligned), and a grid of analysis squares is overlaid on both. Squares are then processed with colorimetric image analysis algorithms that quantify the surface area and/or intensity of staining in specific RGB color channels.

3. Development and application of a predictive model: Outputs of the aforementioned image analysis algorithms are used as predictors for a regression model. The model is trained to predict the percentage of cancerous epithelium within each analysis square. The whole-slide images are automatically annotated by application of threshold to the output of the model to select an appropriate label of cancer vs. non-cancer for each analysis region within the image. Prospective application of the trained model results in the automated delineation of PCa on each WSI.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 4A-4J are images showing examples of pseudo-color outputs of image analysis algorithms from which the predictive features were calculated.

DETAILED DESCRIPTION

Figure 1:
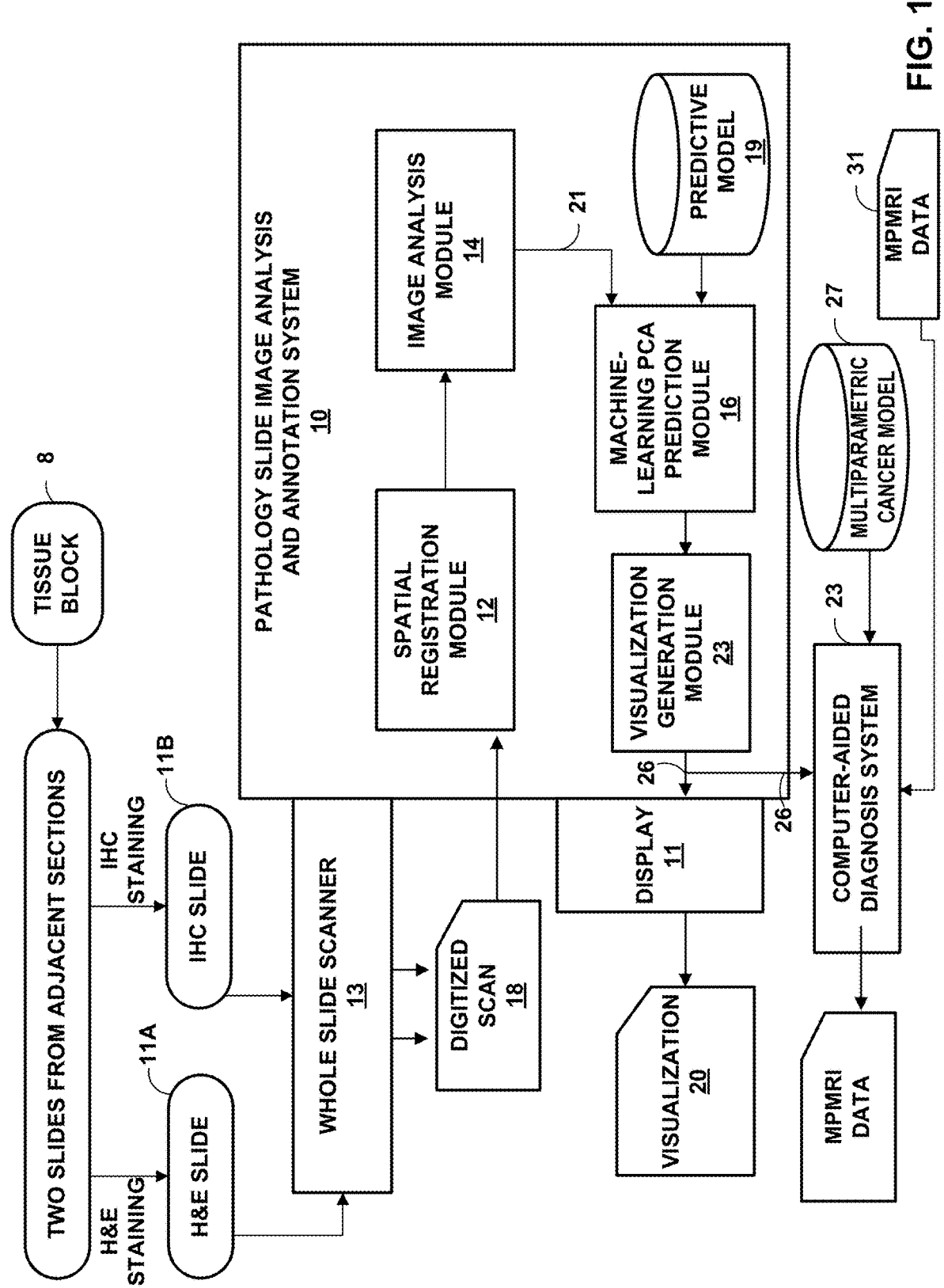
FIG. 1 is a block diagram illustrating an example medical imaging analysis system configured in accordance with one or more techniques of the present disclosure.

FIG. 1 is a block diagram illustrating an example pathology slide image analysis and annotation system 10 ("system 10") in accordance with one or more techniques of the present disclosure. In the example of FIG. 1, system 10 may be a computer-aided diagnosis (CAD) system, a computing device or computing system, such as a mobile computing device (e.g., a smartphone, a tablet computer, a personal digital assistant, and the like), a desktop computing device, a server system, a distributed computing system (e.g., a "cloud" computing system), or any other device configured to receive medical imaging data 18 (e.g., a digitized scan of blocks of tissue) and perform the techniques described herein. In other examples, system 10 may be a slide scanner, medical imaging device or other device having a computing platform configured to implement the techniques described herein.

As described herein, system 10 receives digitized scans of slides of human tissue (e.g., prostate tissue) and applies predictive models to generate predictive prostate cancer determinations and visualizations for use in medical diagnosis, medical research, medical testing, or other fields. In accordance with the techniques described herein, system 10 may receive as input, medical imaging data (e.g., digitized scans of blocks of tissue), such as digitized scan 18, and provide one or more visualizations (e.g., results 20) that indicate predicted cancer.

As shown in the example of FIG. 1, system 10 includes spatial registration module 12, image analysis module 14, PCa prediction module 16 and visualization generation module 23. Each of modules 12, 14, and 16 may be hardware, firmware, software, or some combination thereof. When implemented in software, modules 12, 14, 16 and 23 comprises software instructions that execute on one or more programmable processors of system 10.

In the example of FIG. 1, tissue block 8 is first obtained, such as from prostate specimens obtained from radical prostatectomy (RP). Adjacent sections of tissue blocks are then cut into pairs of slides 11, with each pair having a slide stained with hematoxylin & eosin (H&E) and a second slide for immunohistochemical (IHC) analysis. H&E staining offers information about tissue morphology and architecture. IHC is used to capture protein expression profiles of the cells, which provides functional information that can inform disease likelihood. As examples, a set of slides 11 prepared from adjacent tissue may include a first slide 11A is stained with hematoxylin & eosin (H&E), and a second slide 11B with an immunohistochemical (IHC) antibody cocktail such as alpha-methylacyl CoA racemase (AMACR), high-molecular weight cytokeratin (HMWCK), and p63.

Whole slide scanner 13 digitizes stained slides to create digitized scan 18 (e.g., a digital whole-slide image (WSI)). Digitized scan 18, in various examples, may be data that represents one or more images of tissue of patient. That is, digitized scan 18 may be generated by a medical imaging device, such as whole slide scanner 13. As one example, digitized scan 18 may represent various two-dimensional (2D) images of digitized slides of ex vivo prostate specimens.

Spatial registration module 12 registers (spatially aligns) corresponding adjacent H&E and IHC WSIs. Spatial registration module 12 may, in some examples, process the image data to overlay a grid of analysis regions on digitized scan 18.

Image analysis module 14, in the example of FIG. 1, is configured to receive and process the aligned digitized scan to produce data 21 indicative of various characteristics of the spatially aligned, digitized scans 18. Image analysis module 14 may, for example, processes the analysis regions with one colorimetric image analysis algorithms to produce output data 21. The colorimetric image analysis algorithms may, for example, produce output data 21 that quantifies a surface area and/or intensity of staining of tissue represented in the digitized scans according to specific RGB color channels. In this way, stained tissue sections 8 digitized by whole-slide imaging systems 13 at high resolution are processed and analyzed by image analysis algorithms of image analysis module 14 to extract and assess features such as stain intensity and nuclei density, which relate to the likelihood of disease being present.

Predictive model module 16 receives the output data 21 generated by the image analysis algorithms of image analysis module 14 and processes the data according to predictive model 21 to compute predictors for PCa. As further described herein, predictive model 21 may be a machine learning-based predictive model trained to predict the percentage of cancerous epithelium within each analysis region targeted by spatial registration module 12 within digitized scans 18. In other words, data 21 generated by image analysis module 14 characterizing these features can be used to build predictive model 19 to estimate the spatial distribution of disease on each whole-slide image (WSI), in effect automating the annotation process.

Visualization generation module 23 provides output image data 26 for display as one or more visualizations (e.g., results 20) that indicate predicted cancer. In one example, visualization generation module 23 applies thresholding to respective the estimated predictors computed by machine-learning PCa for each analysis region so as to obtain a binary label of cancer vs. non-cancer for each region. Based on the results, visualization generation module 23 of pathology slide image analysis and annotation system 10 constructs and outputs visualization 20 to provide an indication of whether the imaged tissue has predicted cancer to produce a visualization 20 on display 11. As one example, visualization generation module 23 may create an overlay image for digitized scan 18 that shows and identifies regions of the imaged tissue that are predicted to be cancer. The overlay may, in some examples, visually depict areas of the tissue that are predicted to be cancer based on the output of PCa prediction module 16. In this way, application of the trained predictive model 19 results in the automated delineation of PCa on each WSI.

Output data 26 rendered as visualization 20 may, in some examples, be a 2D or 3D graphical representation of the imaged tissue, with visual indications of cancer regions (e.g., cancer lesions). In some examples, visualization 20 may be output for display, such as at a display device 11 operatively coupled to analysis system 10. In other examples, visualization 20 may be output to one or more other devices for further processing, storage, and/or display.

Prostate adenocarcinoma, which currently comprises >90% of all prostate cancers, is histologically defined simply by the presence of glands without the outer basal cell layer. However, automatically generating accurate annotation of PCa is challenging. PCa tends to be locally infiltrative, and distinguishing malignant glands from surrounding benign glands can be tedious. The presence of the basal cell layer is often difficult to ascertain on H&E alone, which leads to underdiagnosis. Additionally, as recognized by this disclosure, there are several pathologic entities that are mimics of PCa. The most prominent of these is prostatic intraepithelial neoplasia (PIN). While PIN itself is considered benign, high-grade PIN (HGPIN) is suggestive of the presence of invasive carcinoma. To further complicate matters, HGPIN is difficult to distinguish from intraductal carcinoma of the prostate (IDC-P), which is a malignant entity that usually represents the invasion of PCa into benign glands. IHC staining can be used in aiding pathologic diagnosis of PCa. As one example, the triple antibody cocktail specific for high-molecular weight cytokeratin (HMWCK), p63, and α-methylacyl CoA racemase (AMACR) can be used. HMWCK and p63 are basal cell markers that act as negative cancer markers, i.e., the lack of immunoreactivity is indicative of the absence of the basal cell layer. On the other hand, AMACR is a positive cancer marker that is usually highly overexpressed in PCa as well as HGPIN and IDC-P. The combination of these three IHC markers can be, therefore, superior for demonstrating presence of PCa than any of them individually.

As such, in some example implementations, pathology slide image analysis and annotation system 10 enables automated annotation of PCa on digitized whole slide images of prostatectomy specimens stained with H&E and the triple-antibody cocktail of HMWCK+p63+AMACR. In one example, the techniques described herein uses an indirect method of IHC staining. In this example, the IHC cocktail contains the primary antibodies against HMWCK, p63, and AMACR (more specifically, against certain antigens, i.e., peptide fragments that are specific to each protein). Detection utilizes secondary antibodies that bind the primary antibodies. The secondary antibodies themselves are conjugated to linker molecules that recruit the chromogens (DAB and Fast Red) that are actually visualized on the slides, as discussed below.

Image analysis module 14 extracts features from colorimetric image analysis of both H&E slides 11A and IHC slides 11b and stores the data as an aggregate data set for slides from tissue block 8. Predictive model 19 is trained to predict the extent and distribution of cancerous epithelium within each slide 11.

In some examples, the systems and techniques described in this disclosure provide technical solutions that enable the expansion of ground truth data, which in turn increases the amount of modeling data available for training computer-aided diagnosis (CAD) systems models 25. For example, output of visualization generation module 23 may be used a labeled training data for training computer-aided diagnoses system 23, which is an CAD system configured to process multiparametric magnetic resonance imaging (mpMRI) data 31 according to mpMRI cancer model 27 to render predictive prostate cancer visualizations 29.

In general, training cancer predictive models 27 employed for CAD system 23 can require a large amount of modeling data with correlated ground truth (i.e., the true pathologic state of the prostate). The systems and techniques described in this disclosure provide technical solutions in which pathology slide image analysis and annotation system 10 generates output data 26 for use as ground truth training data (labelled data representing known pathologic state of prostate tissue) by automation of the process of cancer annotation of ex vivo prostatectomy specimens, saving significant time compared with manual annotation while achieving cancer detection accuracy comparable to that of a trained pathologist. Further, the systems and techniques described in this disclosure provide technical solutions that enable the expansion of ground truth data, which in turn increases the amount of modeling data available for training CAD models. Example CAD systems and techniques for predicted prostate cancer visualization using quantitative mpMRI models developed are described in U.S. Pat. No. 9,858,665 (application Ser. No. 15/089,273), issued on Jan. 1, 2018, and U.S. Provisional Patent Application No. 62/788,230 filed Jan. 4, 2019, the entire content of each of which is incorporated by reference herein.

Figure 2:
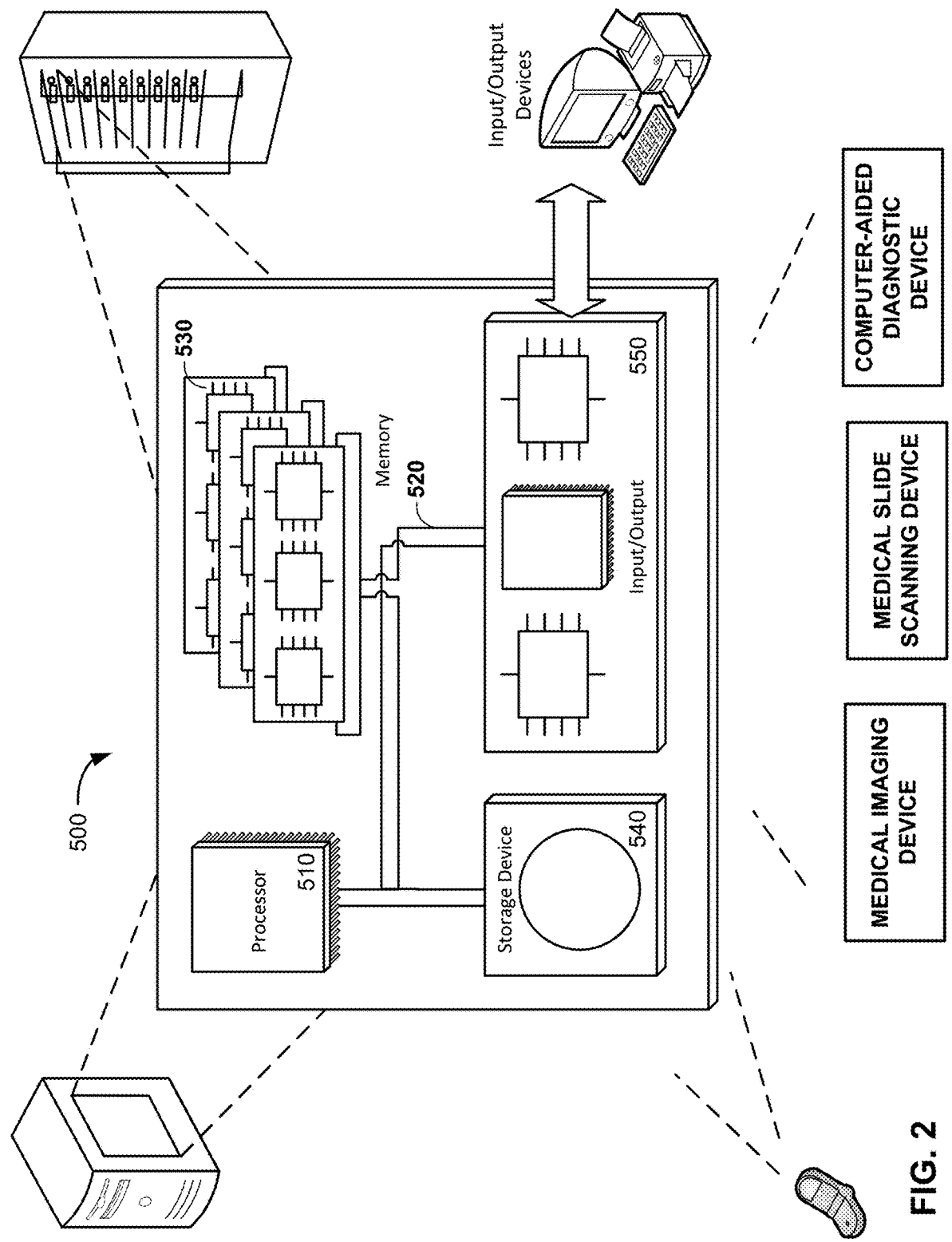
FIG. 2 is a block diagram illustrating an example of various devices that may be configured to implement one or more techniques of the present disclosure.

FIG. 2 is a block diagram illustrating a detailed example of various devices that may be configured to implement one or more techniques of the present disclosure. That is, device 500 of FIG. 2 provides an example implementation for the pathology slide image analysis and annotation system 10 of FIG. 1. Device 500 may be a computer-aided diagnosis (CAD) system, a slide scanner, a medical imaging device, such as a magnetic resonance imaging (MRI) system, a mobile device (e.g., a tablet, a personal digital assistant, or other mobile device), a workstation, a computing center, a cluster of servers, or other examples of a computing environment, centrally located or distributed, that is capable of executing the techniques described herein. Any or all of the devices may, for example, implement portions of the techniques described herein for generating and outputting predicted prostate cancer visualizations for display.

In the example of FIG. 2, computer-implemented device 500 includes a processor 510 that is operable to execute program instructions or software, causing the computer to perform various methods or tasks, such as performing the techniques for generating and/or using digitized scans of stained blocks of tissue for prostate cancer prediction as described herein. Processor 510 is coupled via bus 520 to a memory 530, which is used to store information such as program instructions and/or other data while the computer is in operation. A storage device 540, such as a hard disk drive, nonvolatile memory, or other non-transient storage device stores information such as program instructions, data files of the multidimensional data and the reduced data set, and other information. The computer also includes various input-output elements 550, including parallel or serial ports, USB, Firewire or IEEE 1394, Ethernet, and other such ports to connect the computer to external devices such a printer, video camera, display device, medical imaging device, surveillance equipment or the like. Other input-output elements include wireless communication interfaces such as Bluetooth, Wi-Fi, and cellular data networks.

The computer itself may be a traditional personal computer, a rack-mount or business computer or server, or any other type of computerized system. The computer, in a further example, may include fewer than all elements listed above, such as a thin client or mobile device having only some of the shown elements. In another example, the computer is distributed among multiple computer systems, such as a distributed server that has many computers working together to provide various functions.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media, which includes any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable storage medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

As described herein, pathology slide image analysis and annotation system 10 performs automated or semi-automated analysis and annotation of post-surgical prostate specimens 8 for PCa. Pathology slide image analysis and annotation system 10 enables detailed assessment of disease characteristics and, in some example implementations, automates supply of labeled output data 26 for use as ground truth data for developing and training multiparametric cancer models 25 of computer-aided diagnosis (CAD) systems 23 for PCa detection when applied to mpMRT data.

As manual cancer annotation is tedious and subjective, there have been a number of publications describing methods for automating the procedure via the analysis of digitized whole-slide images (WSIs). However, these studies have focused only on the analysis of WSIs stained with hematoxylin and eosin (H&E), even though there is additional information that could be obtained from immunohistochemical (IHC) staining.

This disclosure describes a technical software architecture for automating the annotation of PCa that is based on automated colorimetric analysis of analysis of digitized whole-slide images (WSIs) of tissue stained with hematoxylin and eosin (H&E) and immunohistochemical (IHC) stained WSIs, such as IHC WSIs stained with a triple-antibody cocktail (combination) against high-molecular weight cytokeratin (HMWCK), p63, and α-methylacyl CoA racemase (AMACR). Data 21 produced by the analysis of the WSI combination is used to train predictive model 19 (e.g., a regression model) to estimate the distribution of cancerous epithelium within slides.

Algorithms and Experimental Results

The following sections provide more details on example algorithms and implementations of pathology slide image analysis and annotation system 10 along with experimental results. To demonstrate the techniques, a total of 184 prostate specimens were obtained from a cohort of 63 patients who underwent radical prostatectomy for definitive treatment of biopsy-proven prostate adenocarcinoma at our institution between November 2009 and January 2012. A summary of the patient characteristics is detailed in Table 1.

TABLE 1

Summary of the clinical and pathologic characteristics of the patient cohort.

| Parameter | Data | |
|---|---|---|
| | Training set (n = 10) | Test Set (n = 53) |
| Mean age (yrs) | 61 (range: 55-72) | 63 (range: 47-76) |
| Mean serum prostate specific antigen at time of surgery (ng/mL) | 11.3 (range: 2.5-19.4) | 7.85 (range: 0.40-37.60) |

TABLE 1-continued

Summary of the clinical and pathologic characteristics of the patient cohort.

| Parameter | Data | |
|---|---|---|
| | Training set (n = 10) | Test Set (n = 53) |
| Pathologic Stage | | |
| T2a | 0 | 9 |
| T2b | 0 | 4 |
| T2c | 4 | 26 |
| T3a | 5 | 10 |
| T3b | 1 | 4 |
| Gleason score | | |
| 3 + 3 | 1 | 13 |
| 3 + 4 | 4 | 21 |
| 4 + 3 | 4 | 8 |
| 4 + 4 | 1 | 5 |
| 4 + 5 | 0 | 4 |
| 5 + 4 | 0 | 2 |

Prostate specimens 8 were fixed, paraffin-embedded and sliced into 4 μm-thick axial sections. From each tissue block 8, two sections were selected from tissue levels no more than 100 μm apart and stained for H&E (slide 11A) and the aforementioned triple antibody cocktail (HMWCK+p63+AMACR) (slide 11B), respectively. H&E staining was performed in three batches using routine clinical protocols. IHC staining was performed using a Ventana automated immunostainer platform (Ventana Medical Systems, Tucson, Ariz.). Slides were incubated for 32 minutes with the triple-antibody cocktail containing primary antibodies to the basal cocktail of HMWCK+p63 (monoclonal mouse; clones 34βE12 and 4A4 respectively; prediluted; Ventana, Tucson, Ariz.) and AMACR (monoclonal rabbit; clone 13H4; prediluted; Dako, Glostrup, Denmark). Detection was performed with the Ventana ultraView Universal DAB Detection Kit and ultraView Universal Alkaline Phosphatase Red Detection Kit according to manufacturer's instructions. This was followed by rinsing, counterstaining with hematoxylin, dehydrating, and coverslipping. In summary, HMWCK+p63 expression in benign basal epithelium was demonstrated as brown by 3,3-diaminobenzidine (DAB), AMACR expression in malignant epithelium was demonstrated as red by Fast Red chromogen, and stroma was demonstrated as blue by hematoxylin counterstain.

Both H&E and IHC slides 11A, 11B were digitized at 20× magnification (0.5 μm2/pixel) using a whole slide scanner (Aperio ScanScope CS, Leica Biosystems, Buffalo Grove, Ill.). Digitized H&E WSIs were annotated at the slide-level for PCa using Aperio's ImageScope software (Leica Biosystems, Buffalo Grove, Ill.) and a pen-tablet screen (Wacom Cintiq 22HD, Saitama, Japan). The slide-level annotations were carried out by demarcating the borders of distinct regions of cancer and assigning a Gleason score (GS) to each region (FIG. 1c). Using the same tools, negative annotations, defined as regions containing artifacts of the histological processing (e.g., tissue folds, debris, irregular staining), were demarcated on the IHC WSIs. Regions of negative annotations were ultimately excluded from analysis, and typically comprised no more than 5% of a given slide. Digitized WSIs and annotations were stored and managed as previously described.

Spatial registration module 12 was configured with signature mapping techniques to further process the digitized WSIs. Example details of signature mapping software (referred to herein as "SigMap") can be found in Metzger, G. J. et al. Development of multigene expression signature maps at the protein level from digitized immunohistochemistry slides. PloS one 7, e33520, https://doi.org/10.1371/journal.pone.0033520 (2012), incorporated herein by reference.

Figure 3A:
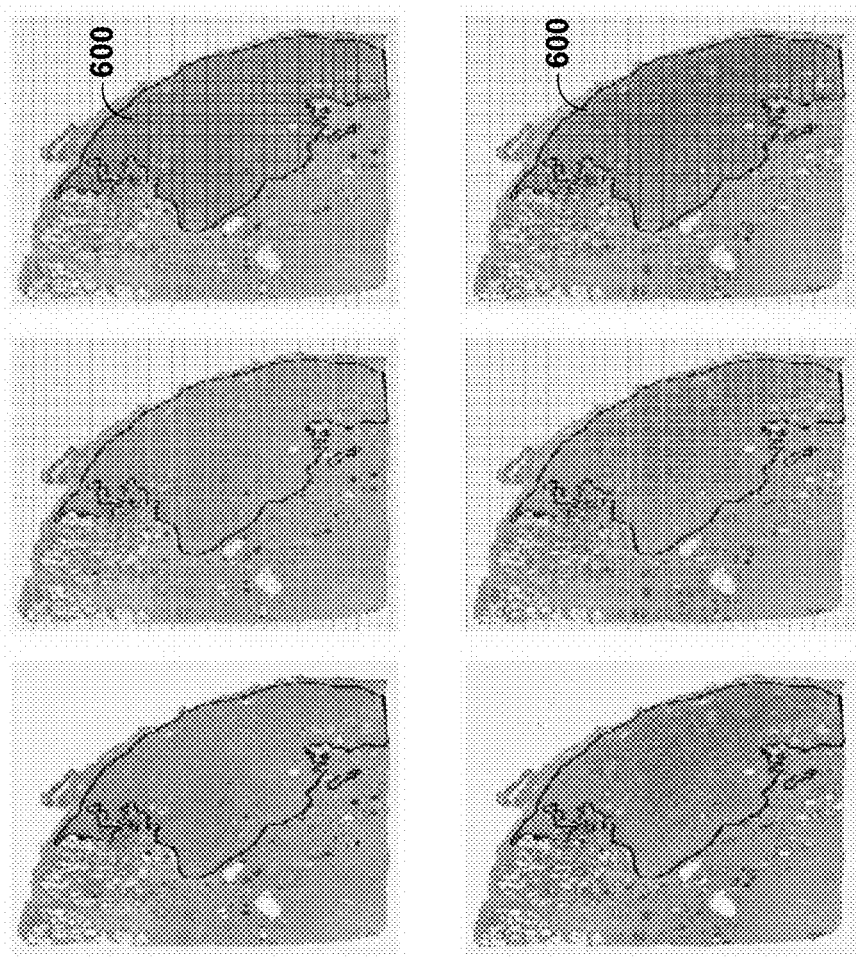
FIGS. 3A-3E illustrate example whole slide images (WSIs) of H&E and IHC slides during initial processing.
Figure 3B:

First, spatial registration module 12 was configured to register the IHC WSI of slide 11B to the H&E WSI of slide 11A using a rigid transformation (FIGS. 3A & 3B). This ensures the accurate spatial co-localization of H&E and IHC WSIs, and in turn the co-localization of image features extracted from both. FIG. 3A shows examples digitized WSIs of slides 11A, 11B. FIG. 3B shows the IHC WSI after rigid registration to the H&E WSI.

Figure 3C:

Next, spatial registration module 12 applied binary masks of the slide-level cancer annotations and the negative annotations to transfer the annotations between H&E WSIs and IHC WSIs (FIG. 3C). FIG. 3C illustrates regions of manually-annotated cancer outlined in black on the H&E WSI (GS 3+4 in this example). These regions were copied to the registered IHC WSI by spatial registration module 12.

Figure 3D:
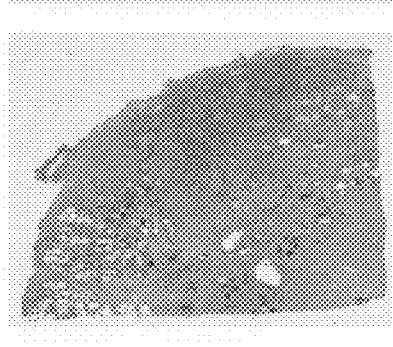
Figure 3E:
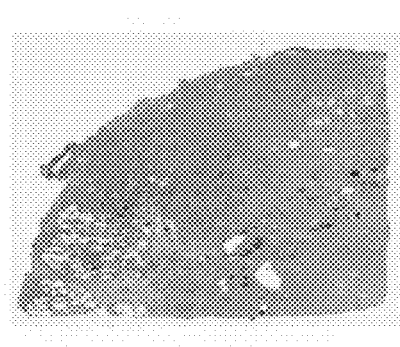
Figure 5A:
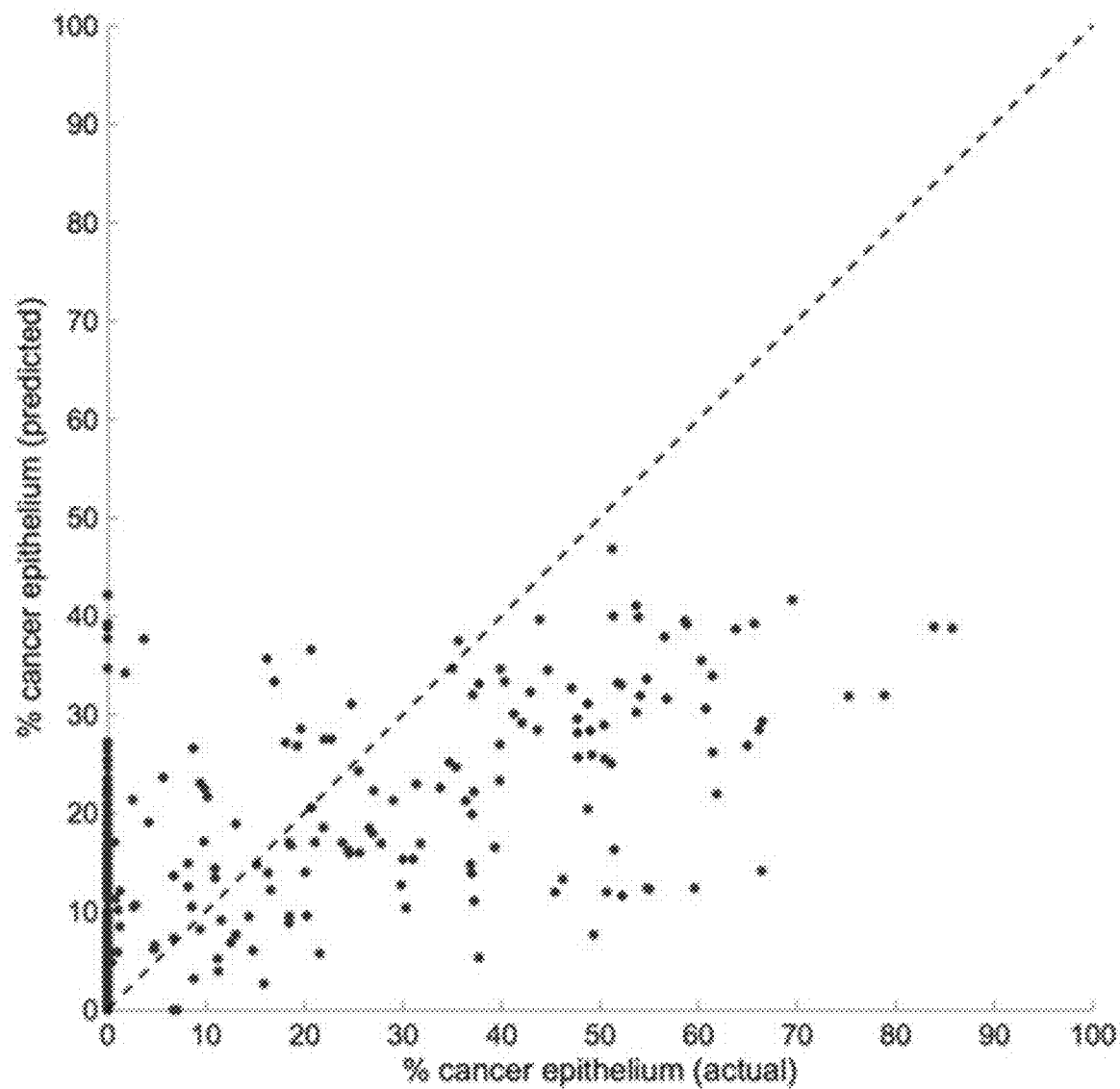
FIGS. 5A-5D a set of cross-validation scatterplots of the predicted vs. actual % cancer epithelium for the four regression models trained with different feature sets. The 400 data points in each plot were accumulated across ten cross validation folds.
Figure 5B:
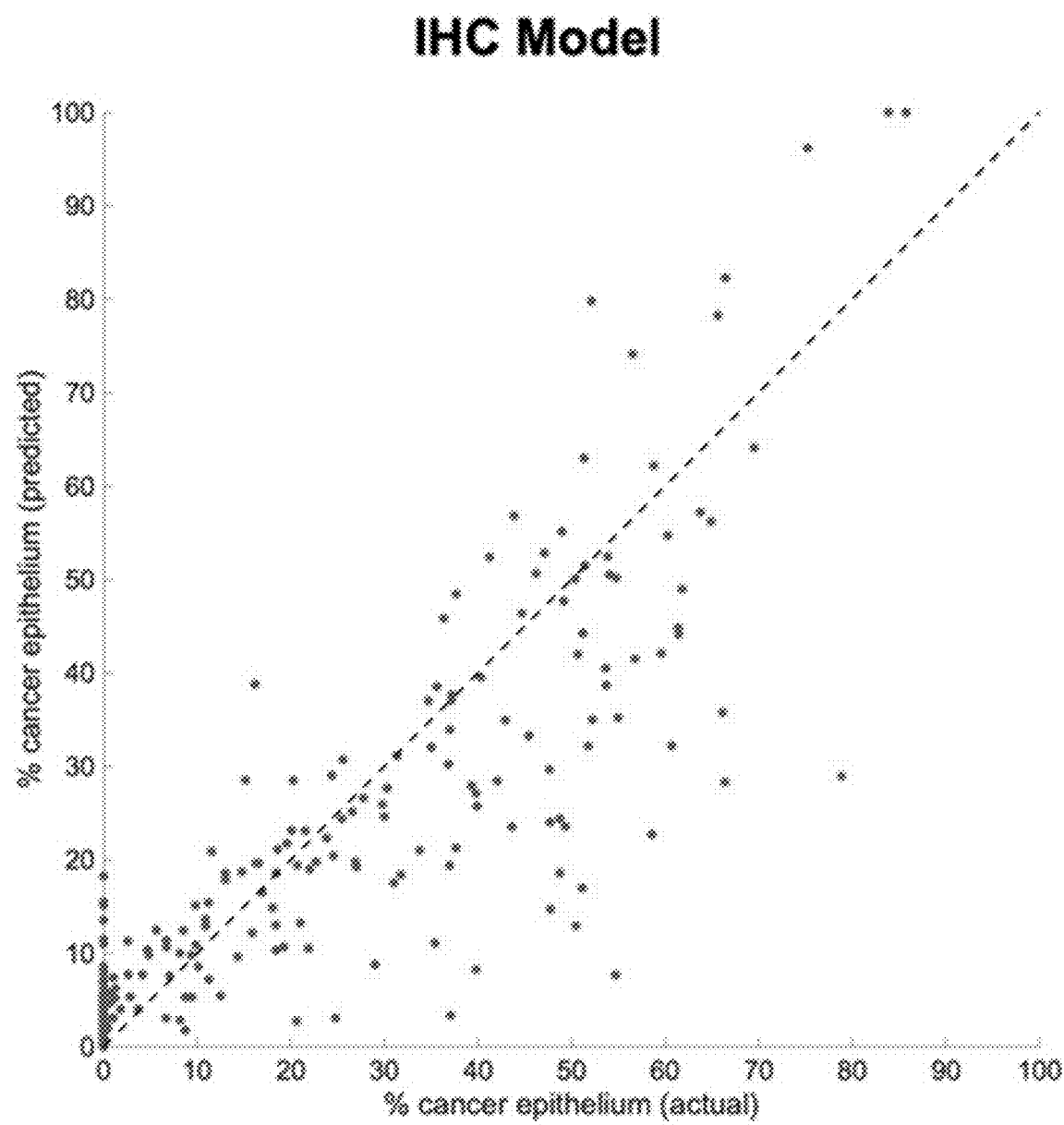
Figure 5C:
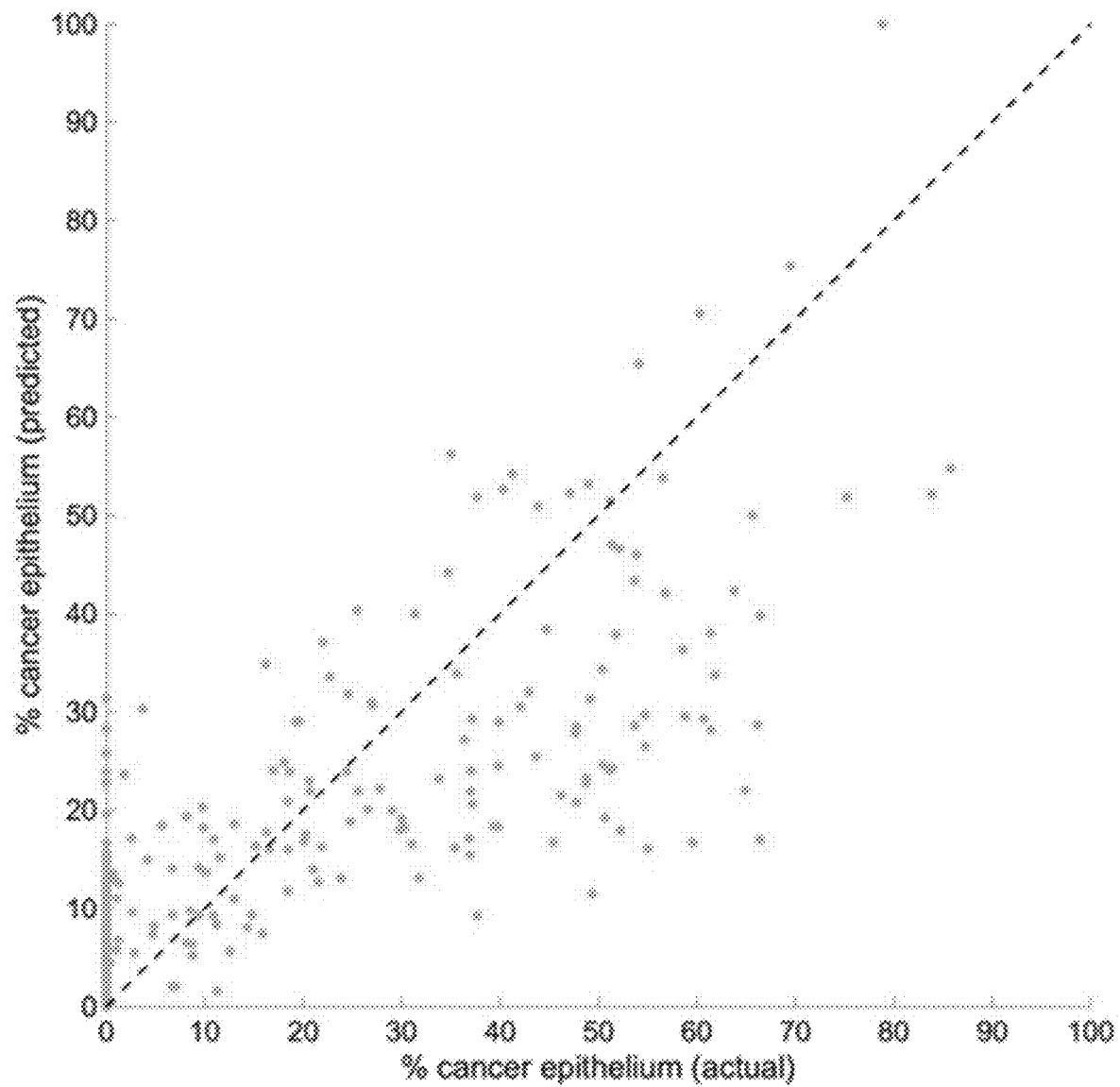
Figure 5D:
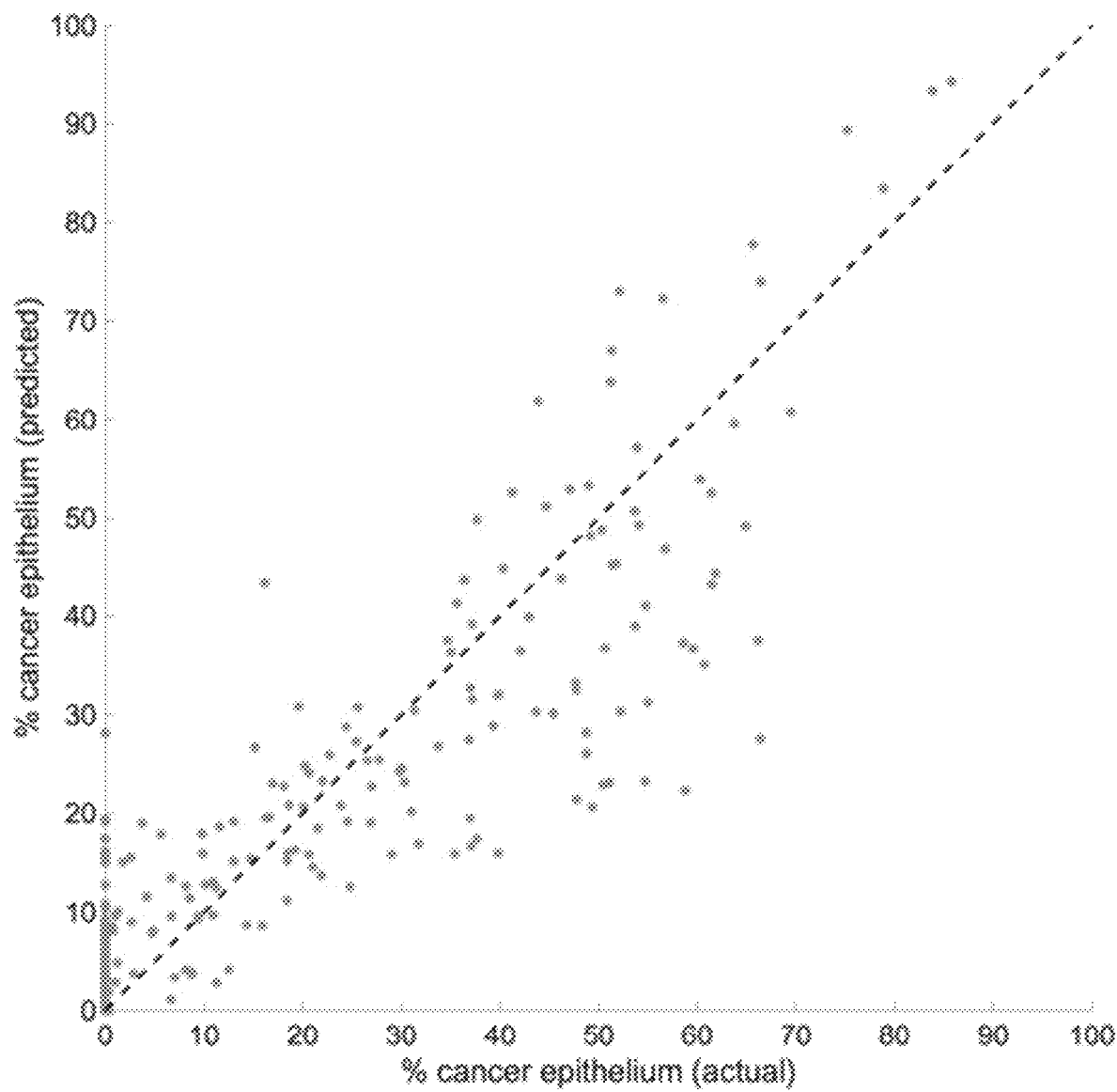
Figure 6A:
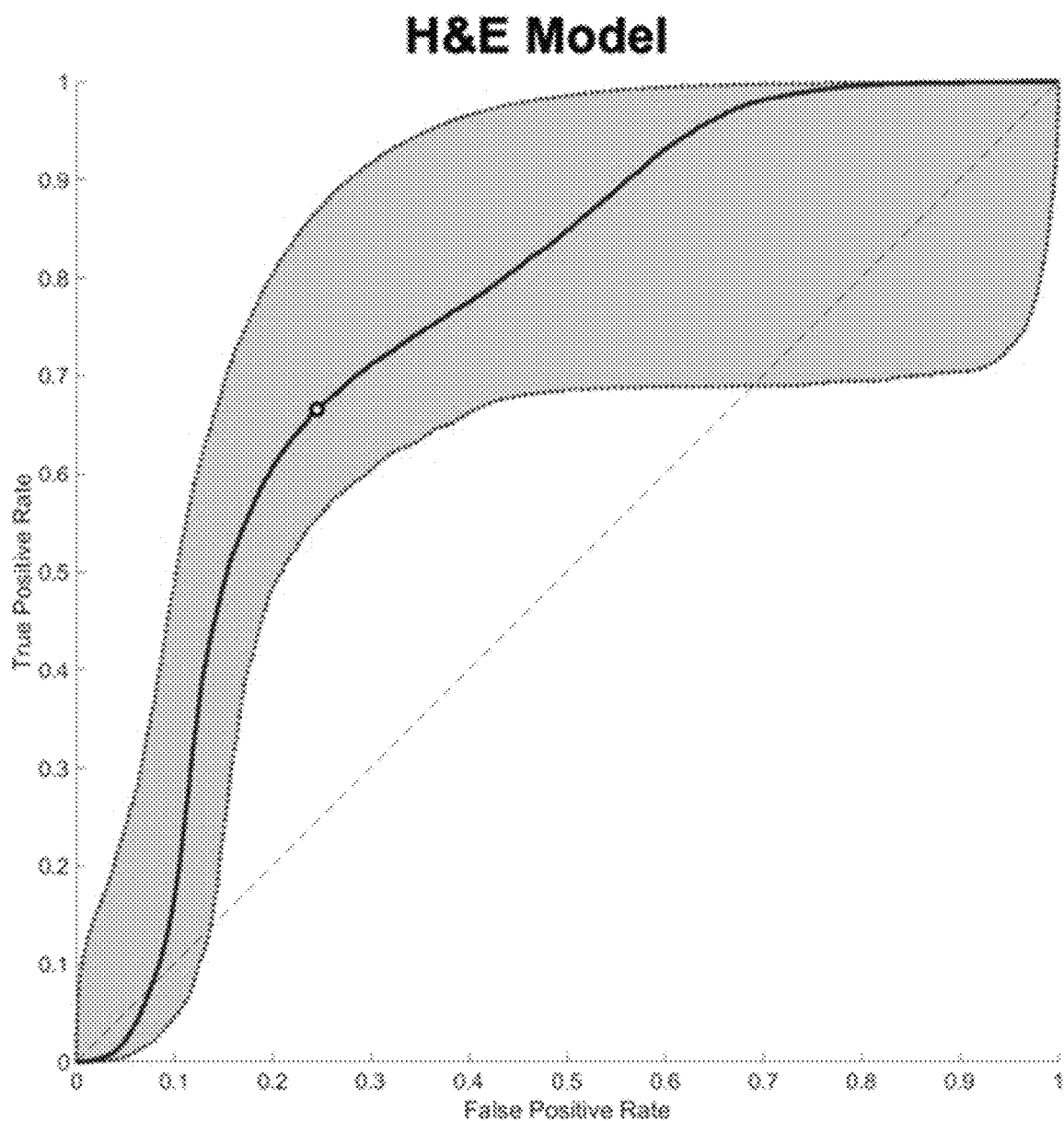
FIGS. 6A-6D are graphs showing the receiver operating characteristic (ROC) curves for the four regression models trained with features derived from H&E and/or IHC slides.
Figure 6B:
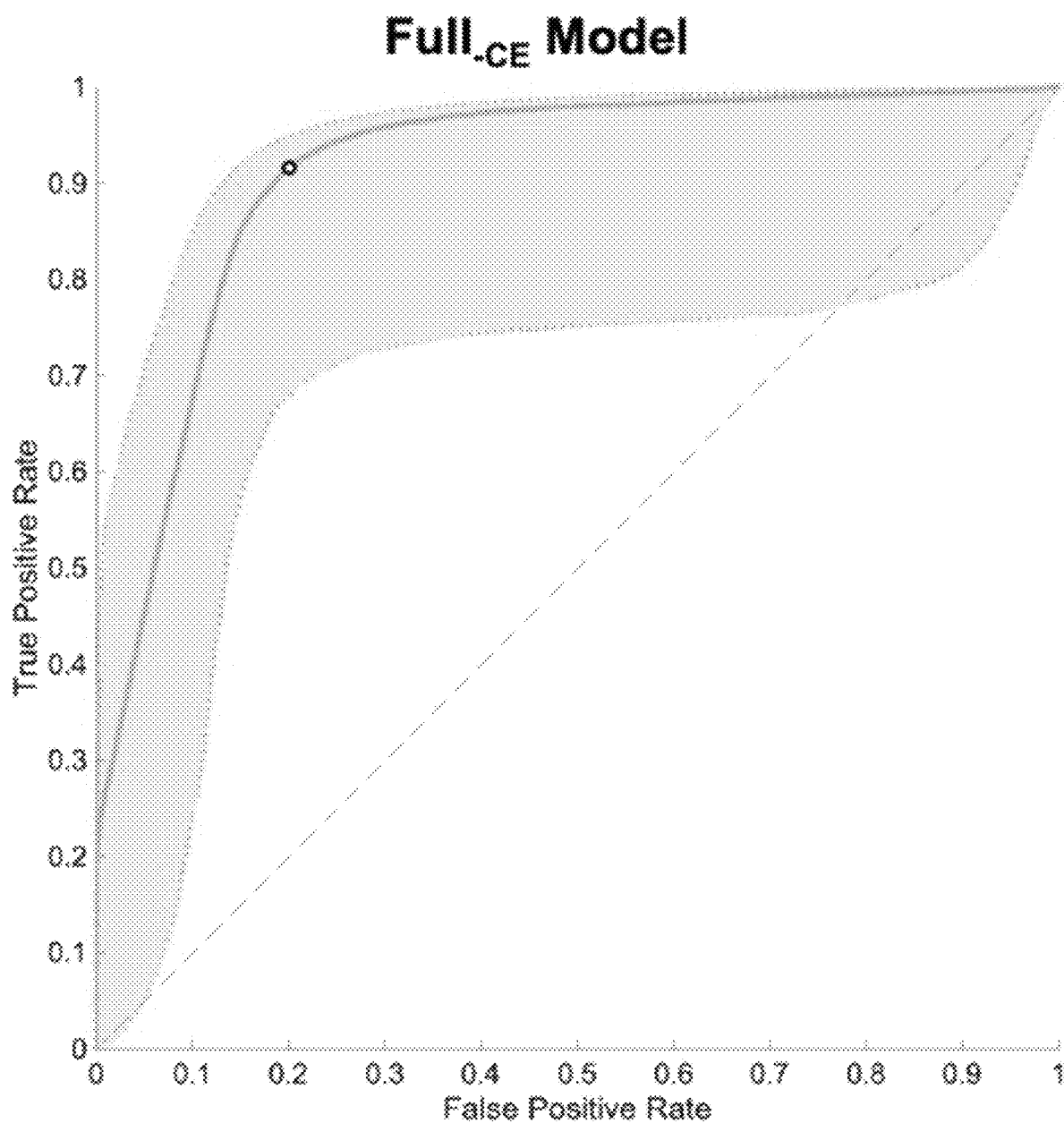
Figure 6C:
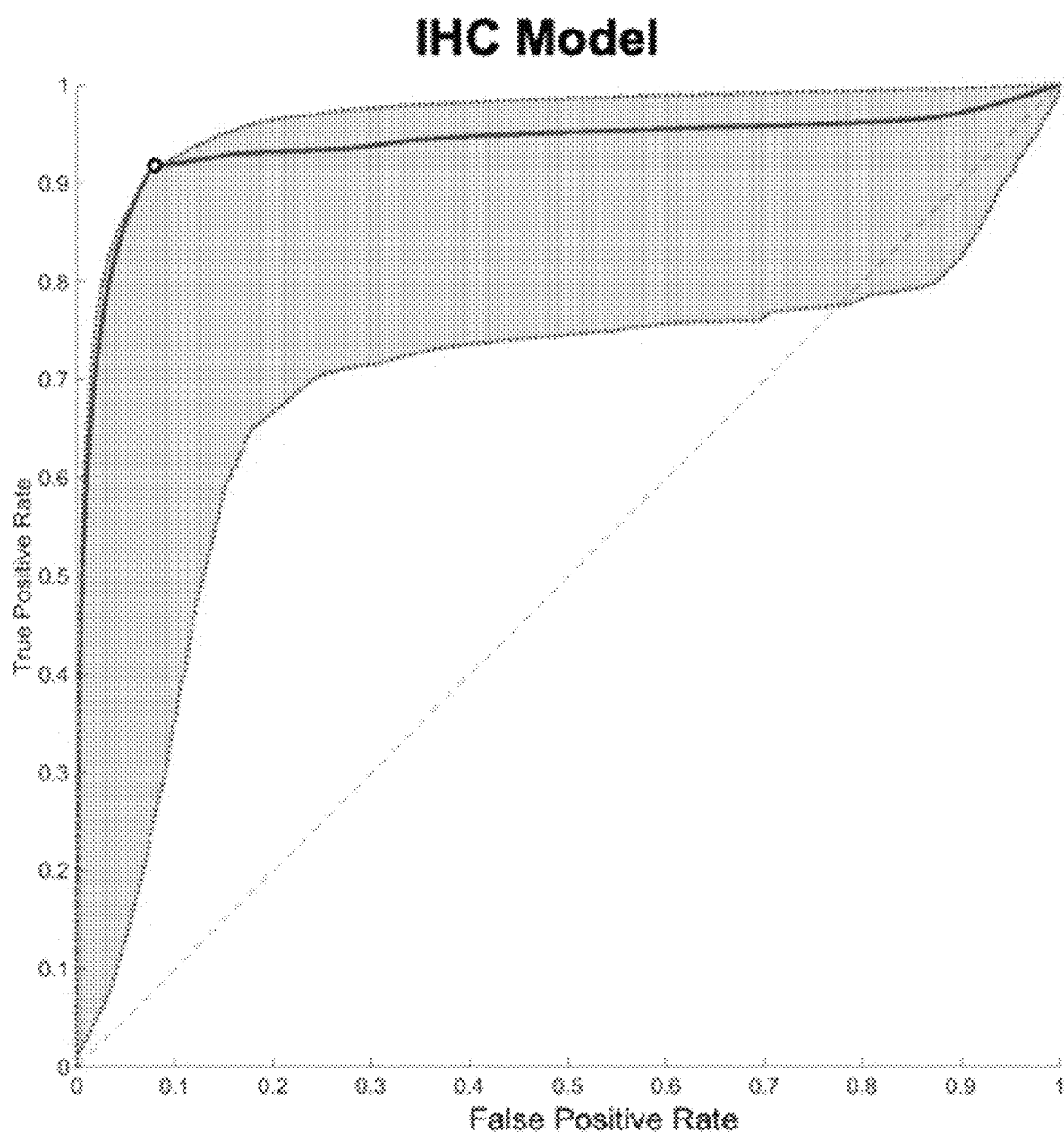
Figure 6D:
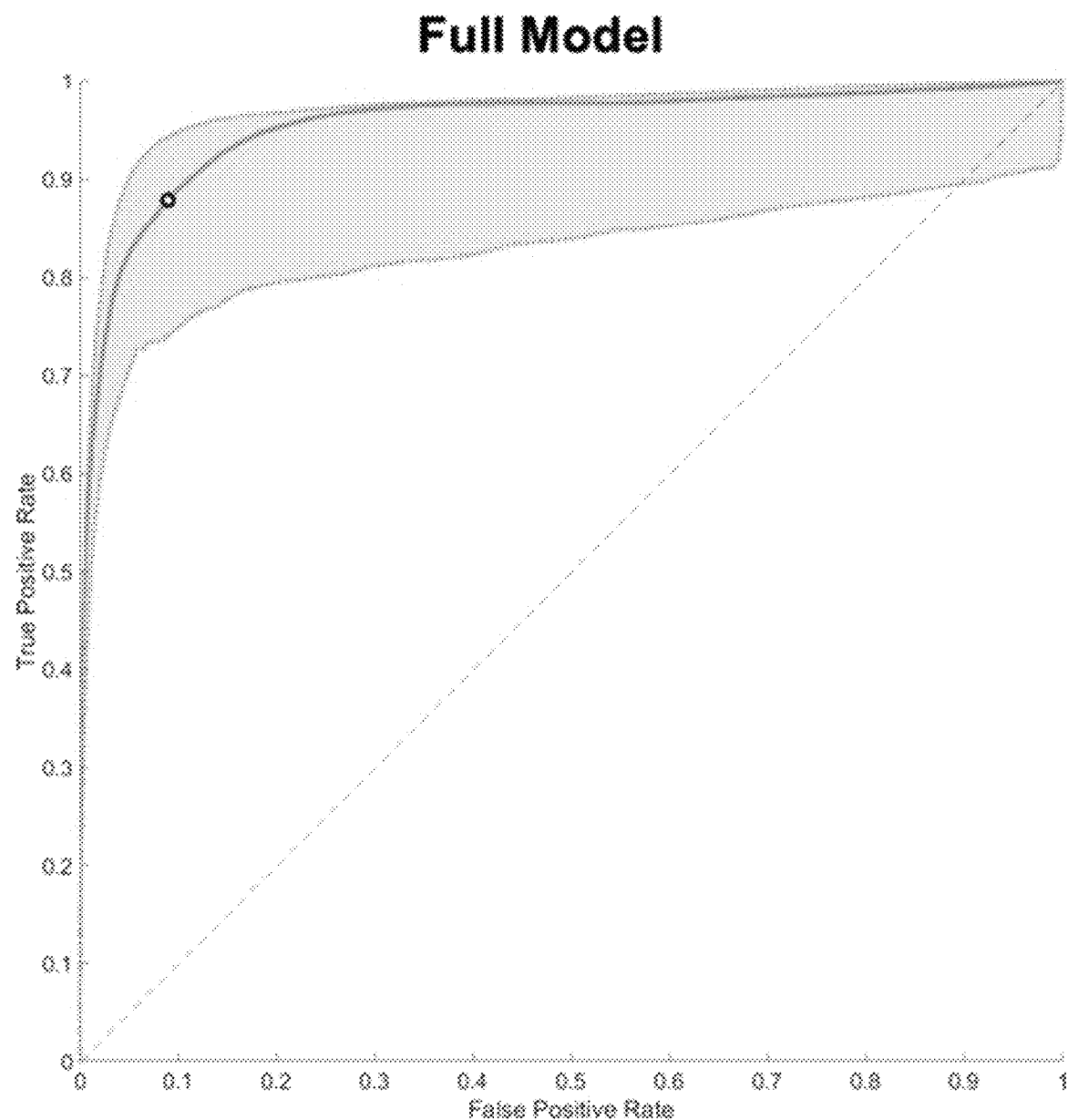

Spatial registration module 12 was further configured to generate a virtual grid composed of 0.25 mm2 analysis squares and modify the image data of the slides to add the grid to the image data for both WSIs for slides 11A, 11B (FIG. 3D). Spatial registration module 12 then labelled as cancer analysis squares 600 whose areas overlapped at least 75% with the cancer annotation mask and assigned the GS of the corresponding annotation (FIG. 3E). Spatial registration module 12 excluded from further analysis squares whose areas overlapped at least 75% with the negative annotation mask.

Image analysis module 14 was configured to implemented three quantitative image analysis algorithms for applied to H&E and IHC WSIs in order to extract features for prediction of cancer.

First, image analysis module 14 was configured to apply a Positive Pixel Count (PPC) algorithm was applied to H&E WSIs of H&E slide 11A. Briefly, the PPC algorithm counts the number of stained pixels within each analysis square that falls within and out of a specified range of hue-saturation-brightness (HSB) color values (positive and negative pixels, respectively). HSB values were sampled from three types of regions that predominantly contained a single histological feature of interest (nuclei, cytoplasm, or stroma). Fifteen of each type of region were manually identified on H&E WSIs and sampled. Ranges of HSB values were calculated for each type of region and were manually adjusted to eliminate overlap between ranges. A separate PPC algorithm was configured for each type of region and its corresponding range of HSB values. The three PPC algorithms were applied to analysis squares, and the resulting numbers of positive pixels were converted to percentages of the analysis square occupied by nuclei, cytoplasm, and stroma (% nuclei, % cytoplasm, and % stroma, respectively), which were in turn used as predictive features. The unstained percentage of each analysis square was also calculated as % unstained=100%−(% nuclei+% cytoplasm+% stroma), and analysis squares with % unstained>99% were excluded from further analysis on the basis that they are taken from regions outside of the tissue boundaries. To account for variations in H&E staining intensity across the three batches, a different set of PPC algorithms was configured and applied to each batch.

Second, image analysis module 14 was configured to apply Color Deconvolution (CD) and Co-expression (CE) algorithms to IHC WSIs of slide 11B to measure the colorimetric features of the IHC stain. Briefly, the CD algorithm isolates individual staining components of IHC WSIs for quantification, while the CE algorithm quantifies how often the staining components occur separately and together. First, three control slides were cut, processed, and singly-stained with either DAB chromogen (brown), Fast Red chromogen (red), or hematoxylin counterstain (blue), using the same protocols as the triple-stained IHC slides described above. The average red-green-blue (RGB) optical density (OD) values of the three components were sampled from the corresponding WSIs of the control slides and were measured as Fast Red (R: 0.283, G: 0.949, B: 0.757), DAB (R: 0.461, G: 0.826, B: 1.0), and hematoxylin (R: 0.21, G: 0.276, B: 0.176). Intensity thresholds were manually configured for each component to define positively-staining pixels, from which the percentage of the analysis square that was positively staining (% Pos) was calculated. As previously described, the OD quantifies the stain intensity, as it is linearly related to the amount of staining.

Third, using the configured RGB OD and intensity threshold values, IHC WSIs were then separated into brown, red, and blue color channels corresponding to each staining component. The brown and red staining were separately quantified by the CD algorithm as previously described. Specifically, the average OD and % Pos were measured by the CD algorithm for both brown and red components, and the products OD*% Pos were calculated and used as predictive features. The co-localization of brown and red staining was quantified by the CE algorithm, which was then used to calculate the percentage of the analysis square that was positively staining for only red or only brown, but not both (% PosCE). % PosCE for red and brown components were used as predictive features. In total, seven features were extracted from each analysis square (Table 2). The features derived from H&E WSIs were the percentages of nuclei, cytoplasm, and stroma, while the features derived from IHC WSIs were the percentages and stain intensities (quantified by the OD) of brown and red staining, which corresponded to the characteristics of the basal cell staining (HMWCK+p63) and the AMACR staining, respectively.

TABLE 2

Summary of the extracted features used for the predictive model. Features are calculated on an analysis-square level.

| Feature | Source | Algorithm |
| --- | --- | --- |
| % Nuclei | H&E | Positive Pixel Count (nuclear) |
| % Cytoplasm | H&E | Positive Pixel Count (cytoplasmic) |
| % Stroma | H&E | Positive Pixel Count (stromal) |
| OD × % Pos (brown) | IHC | Color Deconvolution (brown) |
| OD × % Pos (red) | IHC | Color Deconvolution (red) |
| % $Pos_{CE}$ (brown) | IHC | Co-expression |
| % $Pos_{CE}$ (red) | IHC | Co-expression |

Training data and analysis square-level annotations: during the experimental implementation, ten of the 184 pairs of WSIs were randomly selected for training data for training predictive model 19 as a regression model. Forty analysis squares were randomly selected from each (400 analysis squares in total) and were manually annotated in much greater detail than usual (SCS). The analysis square-level annotations were carried out by meticulously delineating the benign and cancerous epithelium, gland lumens, stroma, and regions of clear glass within each analysis square. The fractional areas of each of the aforementioned components were then summated for each annotated analysis square (FIG. 4b).

FIGS. 2A and 2F illustrate the detail at the level of an analysis square for H&E and IHC WSIs, respectively. In particular, FIG. 4A shows an analysis square from an H&E WSI in the training set (75% overlap with the slide-level annotated cancer in outlined region 605). FIG. 4B shows an analysis square-level annotation of FIG. 4A, with benign epithelium 610 in green color annotation, malignant epithelium 612 in red annotation, gland lumens 614 in a white color annotation, and stroma 616 in a blur color annotation. FIG. 4F illustrates the analysis square corresponding to FIG. 4A taken from the corresponding IHC WSI.

The percentage of cancerous epithelium within each analysis square-level annotation of FIG. 4B was taken to be the ground truth for training predictive model 19. Details on the slides can be found in Table 3.

TABLE 3

| Type | Training (10 total) | Test (174 total) |
|---|---|---|
| Cancer | 84 | 23,757 |
| 3 + 3 | 13 (1) | 2,849 (31) |
| 3 + 4 | 37 (4) | 6,146 (47) |
| 4 + 3 | 34 (4) | 4,452 (22) |
| 4 + 4 | 0 (0) | 2,790 (15) |
| 4 + 5 | 0 (0) | 6,146 (16) |
| 5 + 4 | 0 (0) | 1,374 (4) |
| Benign | 316 | 189,629 |
| Totals | 400 | 213,386 |

Breakdown of the distribution of the analysis squares of the training and test data by cancer presence and Gleason score. An analysis square was labeled cancer if it overlapped at least 75% with the slide-level annotation. Excluded analysis squares (i.e., those that overlapped at least 75% with the negative annotation, or were found to be >99% unstained for H&E staining) are not tabulated here. Numbers in parentheses indicate the number of pairs of WSIs containing cancer with the corresponding Gleason score. Note that some WSIs contained no annotated cancer (1 in the training set, 39 in the test set).

Regression model training and evaluation: elastic net regression models were trained on these data using 10-fold cross validation, with each fold containing the 40 analysis squares from a single pair of WSIs. The elastic net is a generalized linear regression model with both L1 and L2 regularization, and its corresponding objective function to be minimized is:

$$\min_{\omega} \frac{1}{2m} \|X\omega - y\|_2^2 + \alpha\rho\|\omega\|_1 + \frac{\alpha(1-\rho)}{2}\|\omega\|_2^2$$

where m is the number of training examples, n is the number of features, X is the m-by-n matrix of training examples, $\omega$ is the n-by-1 vector of feature weights, y is the m-by-1 vector of labels, and $\alpha$ and $\rho$ are parameters that determine the strengths of the regularization terms.

In one set of experiments, predictive models were trained on four different sets of features: (1) features from H&E WSIs alone (the H&E model), (2) features from IHC WSIs alone (the IHC model), (3) features from both H&E and IHC WSIs, but without the two % PosCE features (the full-CE model), and (4) all features from both H&E and IHC WSIs (the full model). Given the similarity of % Pos from the CD algorithm and % PosCE from the CE algorithm, both the full-CE model and the full model were included in order to test if the inclusion of the two % PosCE features would provide any benefit to cancer identification accuracy.

For each model, the coefficients of the two regularization terms ($\alpha$ and $\rho$) were treated as hyperparameters and selected by cross-validation to maximize the AUC. Trained models were then applied to the analysis squares of the other 174 pairs of slides to produce predicted maps of the distribution of cancerous epithelium. Model outputs were compared to the slide-level annotations on a per-analysis square level using receiver operating characteristic (ROC) curve analysis. Sensitivities and specificities were calculated using the optimum cut-off points for the ROC curves that corresponded to the maxima of the Youden indices. The 95% confidence intervals were calculated using a bootstrap procedure that resampled both WSIs and analysis squares from the training set, and only WSIs from the test set. The 2-sided p-values were found by inverting the 95% bootstrap confidence intervals.

FIGS. 4C-4E and 4G-4I illustrate outputs of colorimetric image analysis algorithms applied by image analysis module 14. In particular, FIGS. 4C-E show sample outputs of the PPC algorithms applied by image analysis module 14. Positive pixels are in red/orange/yellow, and negative pixels in blue. The percentages of positive pixels is taken to be the percentages of the analysis square occupied by nuclei, cytoplasm, or stroma. FIGS. 4G and 4H show sample outputs of the CD algorithm. FIG. 4I shows output of the CE algorithm. As the degree of co-localization between the brown components and the red components of the deconvolved IHC slides is generally small (typically <5% of the analysis square), the overlap is difficult to visualize in FIG. 4I.

FIG. 4J illustrates a table of features computed by image analysis module 14 by application of the image analysis algorithms that PCA prediction module 16 used as inputs for application of predictive model 19.

Quantitative evaluation of model performance: FIGS. 5A-5D are graphs showing evalutation of cross-validation performance for the four models by plotting cumulative scatterplots of predicted % cancer epithelium vs. the actual % cancer epithelium across the 10 cross-validation folds. The cross-validation root mean square error, median absolute error, and maximum absolute error for each model are shown in Table 4.

TABLE 4

| Model | Root mean square error | Median absolute error | Maximum absolute error |
|---|---|---|---|
| H&E model | 15.4 | 8.37 | 52.3 |
| IHC model | 9.36 | 3.55 | 49.9 |
| Full-$_{CE}$ model | 11.9 | 5.59 | 49.4 |
| Full model | 8.37 | 3.09 | 38.8 |

Performance on the test set for the four models was evaluated by plotting the ROC curves. In particular, FIGS. 6A-6D are graphs showing the receiver operating characteristic (ROC) curves for the four regression models trained with features derived from H&E and/or IHC slides. Shaded regions correspond to the 95% bootstrap confidence intervals generated from 1,000 bootstrap samples. Black circles indicate the maxima of the Youden indices, which were chosen as the cutoff points.

The AUC, sensitivity, and specificity of the models are shown in Table 4. In particular, Table 5 provides a comparison of classification performance for the four regression models. Numbers in brackets are the 95% bootstrap confidence intervals generated from 1,000 bootstrap samples. †Significant at p<0.05 compared to the H&E model. *Significant at p<0.05 compared to the full-CE model.

TABLE 5

| Model | AUC | Sensitivity | Specificity |
|---|---|---|---|
| H&E model | 0.755 [0.582, 0.867] | 0.661 [0.562, 0.898] | 0.760 [0.665, 0.803] |
| IHC model | 0.937 [0.692, 0.961] | 0.918 [0.661, 0.931] | 0.920 † [0.780, 0.938] |
| Full$_{cE}$ model | 0.911 [0.682, 0.943] | 0.907 [0.683, 0.924] | 0.809 [0.765, 0.864] |
| Full model | 0.951 † [0.832, 0.964] | 0.871 [0.753, 0.934] | 0.907 †, * [0.894, 0.959] |

The AUC for the full model was significantly higher than that of the H&E model (p=0.026), while the specificity for the full model was significantly higher than those of the H&E and full-cE models (p<0.001 for both). The AUC and specificity for the full model were not significantly different than those of the IHC model (p=0.542 and p=0.108, respectively). The sensitivity of the full model was also not significantly different than those of the H&E, IHC, and full-$_{cE}$ models (p=0.134, p=0.748, and p=0.939, respectively). The CIs of these summary statistics for the full model were notably narrower than those of the other three models, suggesting that the performance of the full model will likely be closer to what is reported here when it is applied prospectively.

For the full model, the sensitivity of PCa detection was broken down by both Gleason score and Gleason grade group (GG), the latter of which may better reflect cancer aggressiveness (Table 6). Using the convention that GG≤2 (GS=3+3 or 3+4) is low to intermediate-grade and GG≤3 (GS 4+3, 4+4, 4+5, or 5+4) is high-grade, the sensitivity of detecting low to intermediate-grade cancers was 0.884, while it was 0.864 for high-grade cancers; this difference was found to be not significant (p=0.107).

TABLE 6

| Type | Number of Analysis Squares | Number Correctly Labeled | Sensitivity |
|---|---|---|---|
| 3 + 3 | 2,849 | 2,411 | 0.846 [0.784, 0.957] |
| 3 + 4 | 6,146 | 5,539 | 0.901 [0.721, 0.954] |
| GG ≤ 2 | 8,995 | 7,950 | 0.884 [0.792, 0.971] |
| 4 + 3 | 4,452 | 4,098 | 0.921 [0.788, 0.956] |
| 4 + 4 | 2,790 | 2,246 | 0.805 [0.732, 0.976] |
| 4 + 5 | 6,146 | 5,135 | 0.836 [0.601, 0.891] |
| 5 + 4 | 1,374 | 1,274 | 0.927 [0.715, 1] |
| GG ≥ 3 | 14,762 | 12,753 | 0.864 [0.727, 0.934] |
| Totals | 23,757 | 20,703 | 0.871 [0.742, 0.929] |

Table 6 shows sensitivity of the full model broken down by Gleason score and Gleason grade groups. Low to intermediate-grade cancers were defined by GG<2 (GS=3+3 or 3+4), and high-grade cancers were defined by GG>3 (GS=4+3, 4+4, 4+5, or 5+4).

Figure 7:
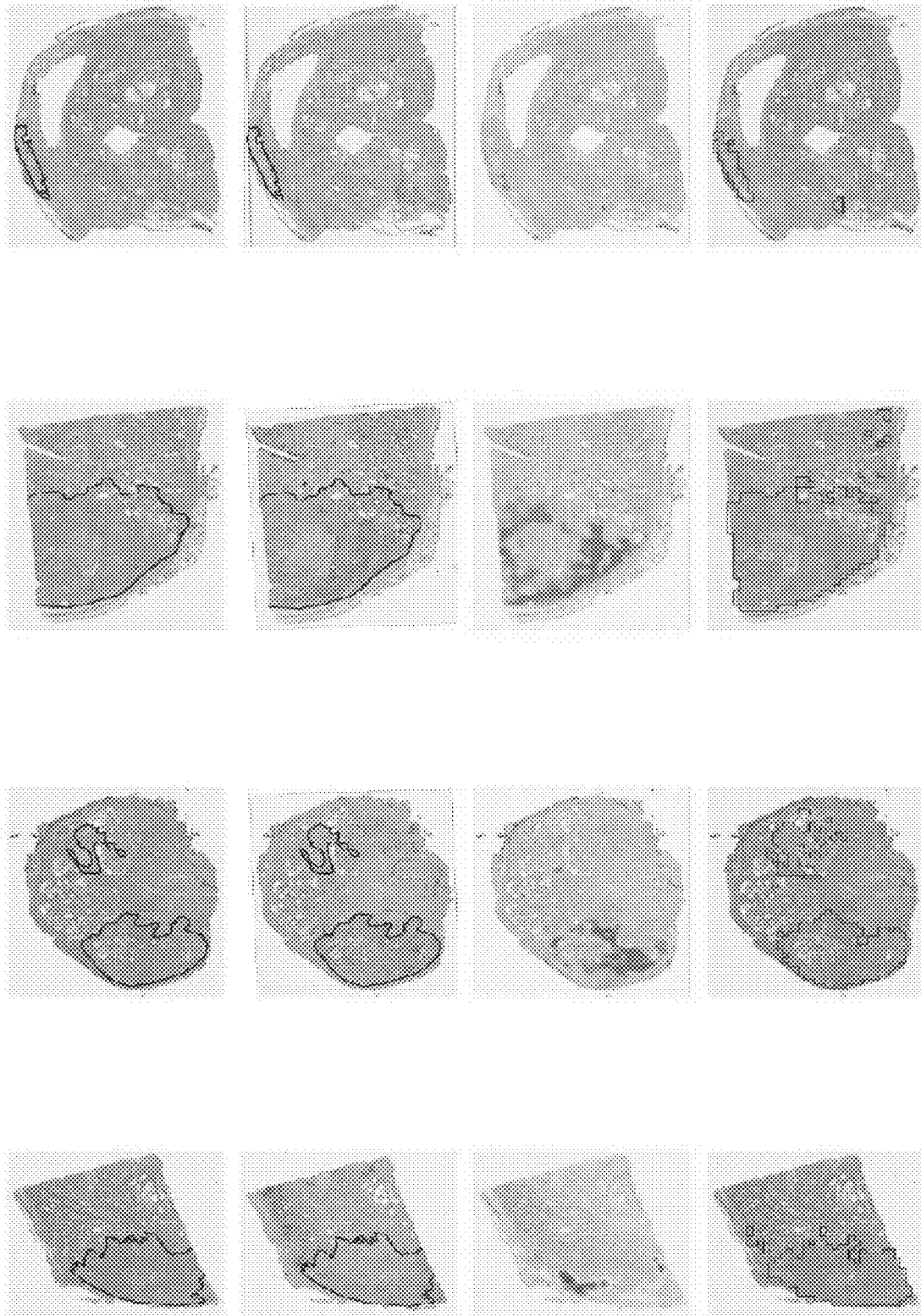
FIG. 7 is set of images showing representative comparisons of manual slide-level annotations to model-generated prediction maps.

Comparison of model-generated annotations to manual slide-level annotations: FIG. 7 is a set of images showing representative H&E and IHC slides with slide-level, manually-annotated cancer by pathologists compared with maps automatically by system 10 using the full model. In particular, FIG. 7 shows representative comparisons of slide-level annotations to model-generated prediction maps produced by PCA prediction module 16. Row 1: H&E WSIs with slide-level annotations outlined in black. Row 2: IHC WSIs corresponding to the H&E WSIs in Row 1. Row 3: Model-generated maps of the predicted distribution of malignant epithelium overlaid on the H&E WSIs. Green/yellow/red indicates low/medium/high density of malignant epithelium, respectively. Row 4: Thresholded versions of prediction maps shown in Row 3. Predicted slide-level annotations are outlined in blue, with internal benign regions outlined in yellow. Note the high degree of correlation between the annotated cancer, distribution of AMACR staining (red on IHC slides), and predicted distribution of malignant epithelium (red on the model-generated maps).

Technical architectures for generating and applying predictive models that use features derived from colorimetric analysis of both digitized H&E and IHC slides has been described herein and demonstrated to be able to detect and delineate PCa on WSIs with accuracy comparable to pathologists' slide-level annotations. The performance of the full model was found to be superior to that of both the H&E and IHC models. The systems and techniques described herein can be modularly integrated into digital pathology frameworks not only for cancer detection, but for grading and assessment of cancer aggressiveness as well as investigating the diagnostic utility of potential genetic markers.

Various examples have been described. These and other examples are within the scope of the following claims.

What is claimed is:

1. A method comprising:
   receiving, by a computing device, a digitized scan comprising whole-slide images of two stained slides of a block of tissue, wherein the digitized scan comprises a first whole slide image of a first slide stained with hematoxylin & eosin (H&E) and a second whole slide image of a second slide stained with an immunohistochemical (IHC) antibody cocktail;
   spatially aligning, by the computing device, the first whole slide image of the first stained slide and the second whole slide image of the second stained slide of the digitized scan;
   overlaying, by the computing device, a plurality of analysis regions on the spatially aligned first whole slide image and the second whole side image of the digitized scan;
   analyzing, by the computing device, one or more of the regions of the spatially aligned first whole slide image and the second whole side image to quantify the staining of the digitized scan;
   processing, by the computing device, the quantified staining of the digitized scan using a predictive model to identify areas of cancer within the digitized scan; and
   outputting, by the computing device, one or more indications of the areas of cancer in the digitized scan.

2. The method of claim 1, wherein overlaying a plurality of regions comprises overlaying on the spatially aligned digitized scan a digital grid of analysis regions comprising of a plurality of squares.

3. The method of claim 1, wherein the predictive model comprises a machine-learning model trained to predict areas of cancer within whole slide images.

4. The method of claim 1, wherein the first slide and the second slide include adjacent sections of tissue from the tissue block.

5. The method of claim 1, wherein spatially aligning, by the computing device, the first whole slide image of the first stained slide and the second whole slide image of the second stained slide comprises:
spatially aligning, by the computing device, the first whole slide image of the first stained slide and the second whole slide image of the second stained slide using a rigid transformation.

6. The method of claim 1, wherein each of the plurality of analysis regions are squares of area 0.25 mm$^2$.

7. The method of claim 1, wherein analyzing, by the computing device, one or more of the plurality of regions of the spatially aligned digitized scans to quantify the staining comprises:
analyzing, by the computing device, one or more of the plurality of regions of the spatially aligned digitized scan to determine at least one of a surface area and an intensity of staining in RGB color channels for each of the one or more of the plurality regions.

8. The method of claim 1, wherein processing, by the computing device, the quantified staining of the digitized scan using a predictive model comprises:
determining, using the predictive model, a percentage of cancerous epithelium within each analysis region; and
determining a binary label of cancer or non-cancer for each analysis region based on a comparison of percentage of cancerous epithelium to a threshold.

9. The method of claim 1, further comprises scanning the two stained slides using a whole slide scanner to create the digitized scan.

10. The method of claim 1, wherein the immunohistochemical (IHC) antibody cocktail contains primary antibodies against alpha-methylacyl CoA racemase (AMACR), high-molecular weight cytokeratin (HMWCK), and p63.

11. An apparatus comprising:
a computer-readable storage medium storing a digitized scan comprising whole-slide images of two stained slides of a block of tissue, wherein the digitized scan comprises a first whole slide image of a first slide stained with hematoxylin & eosin (H&E) and a second whole slide image of a second slide stained with an immunohistochemical (IHC) antibody cocktail; and
a processor coupled to the computer-readable storage medium;
wherein the processor is configured to
spatially align the first whole slide image of the first stained slide and the second whole slide image of the second stained slide;
overlay, by the computing device, a plurality of analysis regions on the spatially aligned first whole slide image and the second whole side image of the digitized scan;
analyze, by the computing device, one or more of the regions of the spatially aligned first whole slide image and the second whole side image to quantify the staining of the digitized scan;
process, by the computing device, the quantified staining of the digitized scan using a predictive model to identify areas of cancer within the digitized scan; and
output by the computing device, one or more indications of the areas of cancer in the digitized scan.

12. The apparatus of claim 11, wherein the plurality of regions comprises a digital grid.

13. The apparatus of claim 11, wherein the predictive model comprises a machine-learning model trained to predict areas of cancer within whole slide images.

14. The apparatus of claim 11, wherein the first whole slide image and the second whole slide image comprise whole slide images of adjacent sections of tissue from the tissue block.

15. The apparatus of claim 11, wherein to spatially align the first whole slide image of the first stained slide and the second whole slide image of the second stained slide, the processor is further configured to:
spatially align the first block of tissue and the second block of tissue in the digitized scan the first whole slide image of the first stained slide and the second whole slide image of the second stained slide using a rigid transformation.

16. The apparatus of claim 11, wherein each of the plurality of squares of the analysis grid are 0.25 mm$^2$.

17. The apparatus of claim 11, wherein to analyze one or more of the plurality of squares of the spatially aligned digitized scan to quantify the staining, the processor is further configured to:
analyze one or more of the plurality of squares of the spatially aligned digitized scan to determine at least one of surface area and an intensity of staining in RGB color channels for each of the one or more of the plurality of squares.

18. The apparatus of claim 11, wherein to process the quantified staining of the digitized scan using a machine-learning algorithm, the processor is further configured to:
determine, using the machine-learning algorithm, a percentage of cancerous epithelium within each of the one or more of the plurality of squares; and
determine a binary label of cancer or non-cancer for each of the one or more of the plurality of squares based on a comparison of percentage of cancerous epithelium to a threshold.

19. The apparatus of claim 11, wherein the immunohistochemical (IHC) antibody cocktail contains primary antibodies against alpha-methylacyl CoA racemase (AMACR), high-molecular weight cytokeratin (HMWCK), and p63.

20. A non-transitory computer-readable storage medium storing instructions that, when executed, cause one or more processors to:
receive a digitized scan comprising whole-slide images of two stained slides of a block of tissue, wherein the digitized scan comprises a first whole slide image of a first slide stained with hematoxylin & eosin (H&E) and a second whole slide image of a second slide stained with an immunohistochemical (IHC) antibody cocktail;
spatially aligning the first whole slide image of the first stained slide and the second whole slide image of the second stained slide of the digitized scan;
overlay a plurality of analysis regions on the spatially aligned first whole slide image and the second whole side image of the digitized scan;
analyze one or more of the regions of the spatially aligned first whole slide image and the second whole side image to quantify the staining of the digitized scan;
process the quantified staining of the digitized scan using a predictive model to identify areas of cancer within the digitized scan; and
output one or more indications of the areas of cancer in the digitized scan.

21. The non-transitory computer-readable storage medium of claim 20, wherein the immunohistochemical (IHC) antibody cocktail contains primary antibodies against alpha-methylacyl CoA racemase (AMACR), high-molecular weight cytokeratin (HMWCK), and p63.

* * * * *